US012661311B2

(12) United States Patent
Kawakami

(10) Patent No.: US 12,661,311 B2
(45) Date of Patent: Jun. 23, 2026

(54) CLEANSING COMPOSITION COMPRISING HYDROXYPROPYL GUAR HYDROXYPROPYLTRIMONIUM CHLORIDE

(71) Applicant: L'OREAL, Paris (FR)

(72) Inventor: Kazumitsu Kawakami, Westfield, NJ (US)

(73) Assignee: L'OREAL, Paris (FR)

( * ) Notice: Subject to any disclaimer, the term of this patent is extended or adjusted under 35 U.S.C. 154(b) by 363 days.

(21) Appl. No.: 18/459,337

(22) Filed: Aug. 31, 2023

(65) Prior Publication Data

US 2025/0073148 A1 Mar. 6, 2025

(51) Int. Cl.

| | |
|---|---|
| ***A61Q 5/00*** | (2006.01) |
| ***A61K 8/36*** | (2006.01) |
| ***A61K 8/44*** | (2006.01) |
| ***A61K 8/46*** | (2006.01) |
| ***A61K 8/60*** | (2006.01) |
| ***A61K 8/73*** | (2006.01) |
| ***A61K 8/81*** | (2006.01) |
| ***A61K 8/86*** | (2006.01) |
| ***A61Q 5/02*** | (2006.01) |

(52) U.S. Cl.

CPC .............. *A61K 8/466* (2013.01); *A61K 8/361* (2013.01); *A61K 8/44* (2013.01); *A61K 8/602* (2013.01); *A61K 8/731* (2013.01); *A61K 8/737* (2013.01); *A61K 8/8152* (2013.01); *A61K 8/86* (2013.01); *A61Q 5/02* (2013.01); *A61K 2800/596* (2013.01)

(58) Field of Classification Search

CPC .......... A61K 8/466; A61K 8/361; A61K 8/44; A61K 8/602; A61K 8/731; A61K 8/737; A61K 8/8152; A61K 8/86; A61K 2800/596; A61K 8/442; A61K 8/604; A61Q 5/02; A61Q 5/12

USPC ........................................................ 510/119

See application file for complete search history.

(56) References Cited

U.S. PATENT DOCUMENTS 6,475,474 B1 11/2002 Ricca
8,658,581 B2 2/2014 Hloucha et al.
9,636,286 B2 5/2017 Grundhofer (Continued)

FOREIGN PATENT DOCUMENTS

BR 112020010785 B1 7/2022
DE 102007001027 A1 7/2008

(Continued)

OTHER PUBLICATIONS

Olaplex No. 4 Bond Maintenance Shampoo, INCI Decoder https://incidecoder.com/products/olaplex-no-4-bond-maintenance-shampoo-2.

(Continued)

*Primary Examiner* — Eisa B Elhilo
(74) *Attorney, Agent, or Firm* — POLSINELLI PC

(57) ABSTRACT

The instant disclosure is drawn to cleansing composition comprising: (a) a plurality of anionic surfactants, for example, a combination of one or more acyl isethionates and one or more acyl amino acids; (b) one or more amphoteric surfactants (c) one or more nonionic surfactants; (d) hydroxypropyl guar hydroxypropyltrimonium chloride; (e) one or more cationic polymers other than a cationic guar; and (f) water, wherein (a), (b), and (c) are in an amount totaling about 15 to about 40 wt. % of the composition. The compositions are useful for cleansing hair while providing improved cosmetic properties to the hair.

20 Claims, 1 Drawing Sheet

B C-3 C-4 C-5 C-6

(56) References Cited

U.S. PATENT DOCUMENTS

| | | | | |
|---|---|---|---|---|
| 10,717,947 | B2 | 7/2020 | Zhang et al. | |
| 11,052,033 | B2 | 7/2021 | Lizarraga et al. | |
| 2002/0155962 | A1 | 10/2002 | Cincotta et al. | |
| 2003/0170296 | A1 | 9/2003 | Sintov et al. | |
| 2005/0158270 | A1 | 7/2005 | Frantz et al. | |
| 2005/0186164 | A1 | 8/2005 | Akyuz | |
| 2005/0226910 | A1 | 10/2005 | Sintov et al. | |
| 2009/0071493 | A1 | 3/2009 | Nguyen et al. | |
| 2009/0214608 | A1 | 8/2009 | Monin et al. | |
| 2011/0245124 | A1* | 10/2011 | Tsaur | A61Q 19/005 510/130 |
| 2011/0245125 | A1* | 10/2011 | Tsaur | A61Q 19/10 510/159 |
| 2014/0308227 | A1 | 10/2014 | Mabille | |
| 2014/0349902 | A1 | 11/2014 | Allef et al. | |
| 2016/0030315 | A1 | 2/2016 | Emiru et al. | |
| 2016/0045424 | A1 | 2/2016 | Schwab et al. | |
| 2016/0120803 | A1 | 5/2016 | Mathur et al. | |
| 2016/0287508 | A1 | 10/2016 | Zhang et al. | |
| 2016/0296449 | A1 | 10/2016 | Kadir et al. | |
| 2017/0304182 | A1 | 10/2017 | Kadir et al. | |
| 2018/0021229 | A1 | 1/2018 | Gasparri et al. | |
| 2018/0116937 | A1 | 5/2018 | Park et al. | |
| 2018/0177708 | A1 | 6/2018 | Lee et al. | |
| 2018/0318195 | A1 | 11/2018 | Blachechen et al. | |
| 2019/0125650 | A1 | 5/2019 | Lee et al. | |
| 2019/0365619 | A1* | 12/2019 | Ceballos | A61K 8/42 |
| 2019/0365623 | A1* | 12/2019 | Botto | A61K 8/817 |
| 2020/0163860 | A1 | 5/2020 | Adamy et al. | |
| 2020/0163861 | A1 | 5/2020 | Mabille et al. | |
| 2020/0170894 | A1* | 6/2020 | Park | A61K 8/466 |
| 2020/0188255 | A1 | 6/2020 | Battermann et al. | |
| 2020/0375876 | A1 | 12/2020 | Arora et al. | |
| 2021/0093541 | A1 | 4/2021 | Desai et al. | |
| 2021/0196591 | A1 | 7/2021 | Venture Morris et al. | |
| 2021/0401716 | A1* | 12/2021 | Gogineni | A61K 8/416 |
| 2023/0063297 | A1 | 3/2023 | Kawakami et al. | |
| 2023/0096297 | A1 | 3/2023 | Botto et al. | |
| 2023/0145870 | A1 | 5/2023 | Sandoval et al. | |

FOREIGN PATENT DOCUMENTS

| | | | | |
|---|---|---|---|---|
| EP | 1642561 | A1 | 4/2006 | |
| EP | 1800715 | A1 | 6/2007 | |
| EP | 2393469 | B1 | 10/2016 | |
| FR | 3113596 | A1 * | 3/2022 | A61Q 19/10 |
| KR | 20210041905 | A | 4/2021 | |
| WO | WO 2020051118 | A1 * | 3/2020 | A61Q 5/02 |
| WO | 2021224509 | A2 | 11/2021 | |

OTHER PUBLICATIONS

Preliminary Search Report and Written Opinion issued on Jun. 4, 2024 for corresponding French Application No. FR 2312022.

* cited by examiner

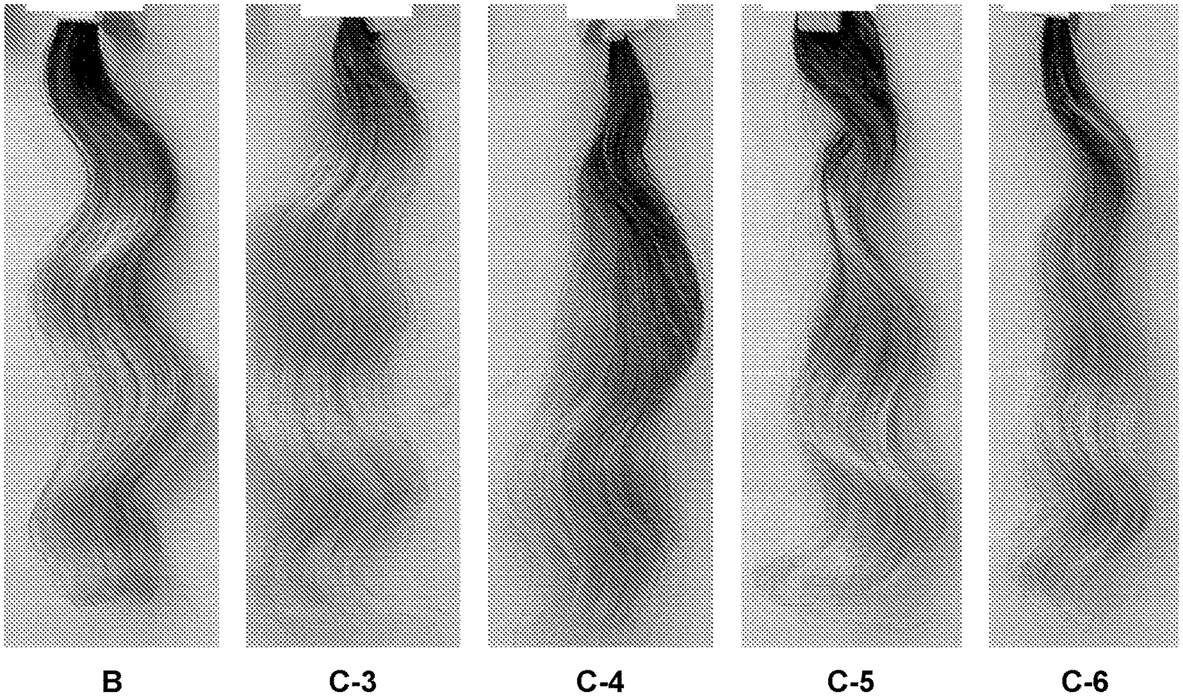
B C-3 C-4 C-5 C-6

CLEANSING COMPOSITION COMPRISING HYDROXYPROPYL GUAR HYDROXYPROPYLTRIMONIUM CHLORIDE

FIELD OF THE DISCLOSURE

The present disclosure is drawn to cleansing compositions comprising hydroxypropyl guar hydroxypropyltrimonium chloride, and to methods for cleansing the hair or body with the compositions.

BACKGROUND

Most "dirt" contains traces of oil and grease, which stick to the surface of the skin and hair. Rinsing with only water is not sufficient to adequately remove the oil and grease. The main functional ingredients in cleansing compositions are surfactants. Surfactants interact with water, thereby allowing it to "wet" surfaces more efficiently. The surfactant-water combination is then able to surround the specks of dirt and carry them away with rinsing. Agitation of the water solution, for example by rubbing hands together during washing or lathering shampoo into hair, also aids the process of removing dirt.

Conventional cleansing compositions such as shampoos, for example, contain surfactants in various amounts. Anionic surfactants are typically included because they provide foaming to a composition. Nonionic surfactants may also be included to provide cleansing, solubilizing, and dispersing properties but are usually less irritating than anionic surfactants. Nonionic surfactants, however, often exhibit less foaming ability and do not provide any enhancement to viscosity (e.g., often a composition is thinner and runnier with increased amounts of nonionic surfactants). In some cleansing applications, higher viscosity is desired for the product's handling or ease of application. In addition, higher viscosity personal care products are more aesthetically appealing to many consumers.

The development of cleansing compositions has been driven by a need for certain performance properties that consumers find desirable. For example, consumers seek cleansing compositions that foam and cleanse well, have a certain "thickness" (viscosity), and are mild to the skin and hair. The cleansing compositions also rinse away from the hair and body with ease. However, the addition of a particular component to a cleansing composition often will enhance one desired property to the detriment of another desired property. It is therefore difficult to achieve a perfect balance of desirable performance properties.

SUMMARY OF THE DISCLOSURE

The present disclosure relates to cleansing compositions that include hydroxypropyl guar hydroxypropyltrimonium chloride, and to methods for cleansing the hair and/or body using the cleansing compositions. The inventor discovered that hydroxypropyl guar hydroxypropyltrimonium chloride is unique in its ability to improve cosmetic properties imparted to hair that is cleansed with the cleansing compositions containing it. In addition, the inventor found that a combination of hydroxypropyl guar hydroxypropyltrimonium chloride and one or more additional cationic polymers other than a cationic guar, such as a cationic cellulose, is particularly beneficial. Hair cleansing compositions containing this combination are particularly effectively for cleansing hair, but they also impart a type of conditioning effect to the hair, for example, resulting in the cleansed hair being less tangled and easier to comb. Hair cleansed with the cleansing compositions require less combing force to detangle than hair cleansed with typical cleansing compositions. Furthermore, hair cleansed with the cleansing composition exhibits improved frizz control, curl definition, and smoothness.

The cleansing composition of the instant disclosure do not require sulfate-based anionic surfactants. Sulfate-based anionic surfactants are commonly used in cleansing compositions due to their robust cleansing ability and foaming properties. They provide abundant, dense, and long-lasting foam during use, which many consumers like. The cleansing compositions of the instant disclosure, however, have excellent foaming properties without sulfate-based anionic surfactants. Evaluation of the compositions' foaming properties showed the foam is abundant, with more than half of the initial foam generated lasting at least 3 minutes after generation. This is impressive and surprising considering the cationic charge of the hydroxypropyl guar hydroxypropyltrimonium chloride and additional cationic polymers, such as cationic celluloses, interferes with the anionic (negative) charge of the anionic surfactants included in the cleansing compositions. It is difficult to not only combine cationic species and anionic species into a single cosmetic composition due to their tendency to interact with one another, but also predict how inclusion of both negative and positively charged species will influence a cosmetic composition, especially cleansing compositions, which require the anionic surfactants for its cleansing properties. Negative interactions between anionic and cationic species can negatively impact viscosity, stability, efficacy, and foaming properties. The inventor found that the cleansing composition disclosed herein, which include hydroxypropyl guar hydroxypropyltrimonium chloride, preferably in combination with a cationic cellulose, overcomes these problems. The cleansing compositions provide abundant and long-lasting foaming during use, despite the lack of sulfate-based anionic surfactants, and hair cleansed with the composition is easier to comb, resists frizzing, and exhibits improved curl definition.

The cleansing compositions typically include:

(a) a plurality of anionic surfactants comprising:
- (a)(i) one or more acyl isethionates, salts thereof, or combination thereof; and
- (a)(ii) one or more acyl amino acids, salts thereof, or combination thereof; (b) one or more amphoteric surfactants;

(c) one or more nonionic surfactants;
- wherein (a), (b), and (c) are in an amount totaling about 15 to about 40 wt. % of the composition, based on a total weight of the cleansing composition;

(d) hydroxypropyl guar hydroxypropyltrimonium chloride;

(e) one or more cationic polymers other than a cationic guar; and (f) water.

Nonlimiting examples of acyl isethionates include sodium isethionate, sodium cocoyl isethionate, sodium lauroyl methyl isethionate, sodium cocoyl methyl isethionate, or a combination thereof.

Nonlimiting examples of acyl amino acids include acyl taurates, acyl glycinates, acyl glutamates, and acyl sarcosinates, salts thereof, or a combination thereof.

As for acyl taurates, nonlimiting examples include sodium cocoyl taurate and sodium methyl cocoyl taurate.

As for acyl glycinates, nonlimiting examples include sodium cocoyl glycinate, sodium lauroyl glycinate, sodium myristoyl glycinate, potassium lauroyl glycinate, potassium cocoyl glycinate, or a combination thereof.

As for acyl glutamates, nonlimiting examples include dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, sodium undecylenoyl glutamate, triethanolamine mono-cocoyl glutamate, triethanolamine lauroylglutamate, and disodium cocoyl glutamate.

As for acyl sarcosinates, nonlimiting examples include potassium lauroyl sarcosinate, potassium cocoyl sarcosinate, sodium cocoyl sarcosinate, sodium lauroyl sarcosinate, sodium myristoyl sarcosinate, sodium oleoyl sarcosinate, sodium palmitoyl sarcosinate, and ammonium lauroyl sarcosinate.

The cleansing compositions include one or more amphoteric surfactants, for example, but not limited to, alkyl amphoproprionates, betaines, alkyl sultaines, alkyl amphoacetates, alkyl amphodiacetates, or a combination thereof. As to alkyl amphoproprionates, nonlimiting examples include cocoamphopropionate, cornamphopropionate, caprylamphopropionate, caproamphopropionate, oleoamphopropionate, isostearoamphopropionate, stearoamphopropionate, and lauroamphopropionate.

As to betaines, nonlimiting examples include coco betaine, cocamidopropyl betaine, lauryl betaine, laurylhydroxy sulfobetaine, lauryldimethyl betaine, cocamidopropyl hydroxysultaine, behenyl betaine, capryl/capramidopropyl betaine, lauryl hydroxysultaine, and stearyl betaine.

As to alkyl sultaines, nonlimiting examples include cocamidopropyl hydroxysultaine and lauryl hydroxysultaine.

As to alkyl amphoacetates, a nonlimiting example is sodium lauroamphoacetate.

Nonionic surfactants are useful in the cleansing compositions. There are numerous nonionic surfactants that may be included. Nonetheless, nonlimiting examples of nonionic surfactants include alkanolamides, alkyl polyglucosides, and alcohols, alpha-diols, alkylphenols and esters fatty acids and/or ethers of fatty alcohols being ethoxylated, propoxylated, or glycerolated and having at least one fatty chain, preferably from 8 to 18 carbon atoms. In preferred embodiments, at least one of the one or more nonionic surfactants is an alkyl polyglucoside.

Nonlimiting examples of alkyl polyglucosides include lauryl glucoside, octyl glucoside, decyl glucoside, coco glucoside, caprylyl/capryl glucoside, and sodium lauryl glucose carboxylate. Typically, at least one alkyl polyglucoside is selected from lauryl glucoside, decyl glucoside, or coco glucoside.

As mentioned above, it is particularly useful to include hydroxypropyl guar hydroxypropyltrimonium chloride and an additional cationic polymer that is not a cationic guar, for example, a cationic cellulose. Nonlimiting examples of cationic celluloses include polyquaternium-4, polyquaternium-10, polyquaternium-24, polyquaternium-67, or a combination thereof.

In various embodiments, the cleansing composition preferably includes one or more water soluble solvents. Nonlimiting examples include glycerin, $C_2$-$C_6$ monoalcohols, polyhydric alcohols, and glycols.

In various embodiments, the cleansing composition preferably includes one or more fatty compounds. Nonlimiting examples include fatty alcohols, fatty acids, C6-C16 hydrocarbons, hydrocarbons containing more than 16 carbon atoms, oils of animal origin, oil of plant origin, hydrocarbon-based oils, synthetic triglycerides, fluoro oils, non-salified fatty acids, fatty acid and/or fatty alcohol esters, and waxes.

In various embodiments, the cleansing compositions preferably include one or more non-cationic thickening polymers. Nonlimiting examples include polysaccharides, polyacrylates, polymethacrylates, polyethylacrylates, polyacrylamides, acrylates/C10-C30 alkyl acrylate crosspolymer, carbomers, hydrophobically modified poly-polyacrylates, hydrophobically modified polyacrylic acids, hydrophobically modified polyacrylamides, acrylamide/ammonium acrylate copolymer, crosslinked polyvinylpyrrolidone (PVP), and sodium acrylate/acryloyldimethyltaurate.

Additional components including miscellaneous ingredients may optionally be included (or excluded) from the cleansing compositions, for example sulfate-based anionic surfactants. Nonlimiting examples of particularly popular sulfate-based surfactants include sodium laureth sulfate and sodium lauryl sulfate. The cleansing compositions are preferably free or essentially (substantially) free from sulfate-based anionic surfactants. In various embodiments, the cleansing compositions preferably include one or more miscellaneous ingredients, for example up to about 10 wt. %, of one or more miscellaneous ingredients. Nonlimiting examples of miscellaneous ingredients include preservatives, fragrances, pH adjusters, salts, chelating agents, buffers, antioxidants, flavonoids, vitamins, botanical extracts, UV filtering agents, proteins, protein hydrolysates and/or isolates, fillers (e.g., organic and/or inorganic fillers such as talc, calcium carbonate, silica, etc.) composition colorants, etc.

The cleansing compositions are particularly useful for cleansing and conditioning hair. The compositions exhibit good cleansing ability, lather, foaming and foam stability, and conditioning properties. Additionally, the cleansing compositions are particularly well-suited for cleansing artificially colored or bleached hair because the compositions preserve the color of the artificially colored hair while simultaneously providing shine, smoothness, moisturization, and frizz control. In preferred embodiments, hair cleansed with the cleansing compositions of the disclosure require less combing force to detangle (or comb) than hair cleansed with a comparative cleansing composition without the hydroxypropyl guar hydroxypropyltrimonium chloride but otherwise identical to the cleansing composition.

BRIEF DESCRIPTION OF THE DRAWINGS

The FIGURE shows hair swatches treated with an inventive cleansing composition and with a comparative cleansing composition.

DETAILED DESCRIPTION OF THE DISCLOSURE

The cleansing composition of the instant case includes hydroxypropyl guar hydroxypropyltrimonium chloride and preferably one or more cationic polymers other than a cationic guar. The one or more cationic polymers are preferably selected from cationic celluloses, preferably polyquaternium-10 (quaternized hydroxyethyl cellulose). The cleansing compositions also do not require sulfate-based anionic surfactants and in various embodiments, the cleansing compositions are preferably free or essentially free from sulfate-based anionic surfactants. Typically, the cleansing compositions include:

(a) about 5 to about 20 wt. % of a plurality of anionic surfactants comprising:
    (a)(i) one or more acyl isethionates, salts thereof, or combination thereof; and
(a)(ii) one or more acyl amino acids, salts thereof, or combination thereof; (b) about 1 to about 10 wt. % of one or more amphoteric surfactants;
(c) about 1 to about 15 wt. % of one or more nonionic surfactants;
    wherein (a), (b), and (c) are in an amount totaling about 15 to about 40 wt. % of the composition,
(d) about 0.1 to about 5 wt. % of hydroxypropyl guar hydroxypropyltrimonium chloride;
(e) one or more cationic polymers other than a cationic guar; and
(f) water;
    wherein all percentages by weight are based on a total weight of the cleansing composition.

Plurality of Anionic Surfactants

For purposes of the instant disclosure, the term “plurality” means “two or more” or “at least two.” In a preferred embodiment, the plurality of anionic surfactants includes three or more anionic surfactants. Also, it is preferred that the cleansing compositions include a plurality of non-sulfate-based anionic surfactants, wherein the cleansing composition is free or essentially free from sulfate-based anionic surfactants, for example, sodium laureth sulfate and sodium lauryl sulfate. Preferably, the plurality of non-sulfate-based anionic surfactants includes one or more acyl isethionates, one or more acyl amino acids, and optionally, a third non-sulfate-based anionic surfactant. More preferably, the plurality of non-sulfate-based anionic surfactants includes one or more acyl isethionates, one or more acyl glycinates, and optionally a third non-sulfate-based anionic surfactant. In a particularly preferred embodiment, the plurality of non-sulfate-based anionic surfactants includes one or more acyl isethionates, one or more acyl glycinates, and a third non-sulfate-based anionic surfactant selected from sodium cocoate, potassium cocoate, mono-, di- or tri-ethanolamine cocoate, or a combination thereof, for example, the plurality of non-sulfate-based anionic surfactants is preferably sodium cocoyl isethionate, potassium cocoyl glycinate, and potassium cocoate.

The amount of the plurality of anionic surfactants in the cleansing composition will vary. Nonetheless, the cleansing composition typically includes about 5 to about 20 wt. % of a plurality of anionic surfactants, preferably a plurality of non-sulfate-based anionic surfactants. In various embodiments, the cleansing composition includes about 5 to about 18 wt. %, about 5 to about 15 wt. %, about 5 to about 12 wt. %, about 6 to about 20 wt. %, about 6 to about 18 wt. %, about 6 to about 15 wt. %, about 6 to about 12 wt. %, about 8 to about 20 wt. %, about 8 to about 18 wt. %, about 8 to about 15 wt. %, about 12 wt. % of the plurality of anionic surfactants, preferably a plurality of non-sulfate-based anionic surfactants. In a preferred embodiment, the cleansing composition include about 5 to about 20 wt. %, and preferably about 6 to about 18 wt. %, and even more preferably about 8 to about 14 wt. % of the plurality of anionic surfactants, preferably a plurality of non-sulfate-based anionic surfactants.

(a) Non-Sulfate-Based Anionic Surfactants

In some embodiments, the non-sulfate-based anionic surfactants are the predominant type of surfactant in the cleansing composition (i.e., there is a higher weight percentage of non-sulfate-based anionic surfactants than any other single surfactant type in the cleansing composition). Useful non-sulfate-based anionic surfactants include, but are not limited to, acyl isethionates, acyl amino acids (such as acyl taurates, acyl glycinates, acyl glutamates, and acyl sarcosinates), alkyl sulfonates, alkyl sulfosuccinates, alkyl sulfoacetates, alkoxylated monoacids, salts thereof, and a combination thereof.

The total amount of the plurality of non-sulfate-based anionic surfactant will vary. Nonetheless, the cleansing composition typically includes about 5 to about 20 wt. %, based on the total weight of the cleansing composition. In further embodiments, the cleansing composition includes about 5 to about 18 wt. %, about 5 to about 15 wt. %, about 5 to about 12 wt. %, about 6 to about 20 wt. %, about 6 to about 18 wt. %, about 6 to about 15 wt. %, about 6 to about 12 wt. %, about 8 to about 20 wt. %, about 8 to about 18 wt. %, about 8 to about 15 wt. %, about 8 to about 12 wt. % of the plurality of non-sulfate-based anionic surfactants, based on the total weight of the cleansing composition.

Acyl Isethionates

Non-limiting examples of useful acyl isethionates include those of formula (I):

(I)

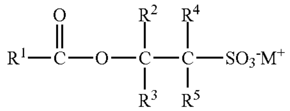

wherein $R^1$ represents a $C_{4-36}$ substituted or unsubstituted hydrocarbyl group; each of $R^2$, $R^3$, $R^4$ and $R^5$ independently represents a hydrogen atom or a $C_{1-4}$ alkyl group and $M^+$ represents a cation. Preferably $R^1$ is selected from a substituted or unsubstituted alkyl, alkenyl, aryl or alkylaryl group. More preferably $R^1$ is selected from a substituted or unsubstituted alkyl or alkenyl group. Most preferably $R^1$ is an unsubstituted alkyl or alkenyl group, especially an unsubstituted alkyl group. Even more preferably $R^1$ represents a $C_{5-30}$ alkyl group, preferably a $C_{7-24}$ alkyl group, more preferably a $C_{7-21}$ alkyl group, most preferably a $C_{7-17}$ alkyl group.

In some embodiments $R^2$ and $R^3$ independently represent a $C_{1-4}$ alkyl group, suitably a $C_{1-4}$ alkyl group in which a propyl or butyl group, when present, is straight-chained. Suitably $R^2$ and $R^3$ may independently represent an n-propyl, ethyl or preferably, a methyl group. However, in preferred embodiments $R^2$ is a hydrogen atom and $R^3$ is a hydrogen atom.

In some embodiments $R^4$ and $R^5$ represents a hydrogen atom and the other represents a hydrogen atom or a $C_{1-4}$ alkyl group. Suitable one of $R^4$ and $R^5$ represents a hydrogen atom or a $C_{1-4}$ alkyl group in which a propyl or butyl group is straight-chain. Preferably one of $R^4$ and $R^5$ represents an n-propyl, ethyl or methyl group or, most preferably, a hydrogen atom. Most preferably both $R^4$ and $R^5$ represent hydrogen atoms.

In especially preferred embodiments each of the $R^2$, $R^3$, $R^4$ and $R^5$ is hydrogen and the isethionate compound is of formula (II)

$$R^1CO_2CH_2CH_2SO_3M^+ \quad \text{(II)}$$

$M^+$ represents an optionally substituted ammonium cation or, most preferably, a metal cation. Suitable ammonium cations include $NH_4^+$ and the ammonium cation of triethanolamine. Suitable metal cations include alkali metal cations, for example sodium, lithium, and potassium cations, and alkaline earth metal cations, for example calcium and magnesium cations. Preferably $M^+$ represents a potassium or sodium cation.

$R^1$ may be an alkyl group or an alkenyl group. Preferably $R^1$ is an alkyl group. $R^1$ is preferably the residue of a fatty acid. Fatty acids obtained from natural oils often include mixtures of fatty acids. For example, the fatty acid obtained from coconut oil contains a mixture of fatty acids including $C_{12}$ lauric acid, $C_{14}$ myristic acid, $C_{16}$ palmitic acid, $C_8$ caprylic acid, and $C_{18}$ stearic and oleic.

$R^1$ may include the residue of one or more naturally occurring fatty acids and/or of one or more synthetic fatty acids. In some preferred embodiments $R^1$ consists essentially of the residue of a single fatty acid.

Examples of carboxylic acids from which $R^1$ may be derived include butyric acid, hexanoic acid, caproic acid, caprylic acid, capric acid, lauric acid, myristic acid, palmitic acid, palmitoleic acid, stearic acid, oleic acid, linoleic acid, arachidic acid, gadoleic acid, arachidonic acid, eicosapentanoic acid, behinic acid, erucic acid, docosahexanoic lignoceric acid, naturally occurring fatty acids such as those obtained from coconut oil, tallow, palm kernel oil, butterfat, palm oil, olive oil, corn oil, linseed oil, peanut oil, fish oil and rapeseed oil; synthetic fatty acids made as chains of a single length or a selected distribution of chain lengths; and mixtures thereof.

Non-limiting examples of specific acyl isethionates include sodium isethionate, sodium cocoyl isethionate, sodium lauroyl methyl isethionate, and sodium cocoyl methyl isethionate. In some embodiments, sodium cocoyl methyl isethionate is a particularly useful acyl isethionate that may be included in the cleansing compositions.

The total amount of the one or more acyl isethionates in the cleansing composition will vary but is typically from about 5 to about 20 wt. % of the one or more acyl isethionates, based on the total weight of the cleansing composition. In further embodiments, the cleansing composition includes about 5 to about 18 wt. %, about 5 to about 15 wt. %, about 5 to about 12 wt. %, about 6 to about 20 wt. %, about 6 to about 18 wt. %, about 6 to about 15 wt. %, about 6 to about 12 wt. %, about 8 to about 20 wt. %, about 8 to about 18 wt. %, about 8 to about 15 wt. %, or about 8 to about 12 wt. % of the one or more acyl isethionates, based on the total weight of the cleansing composition. In a preferred embodiment, the total amount of the one or more acyl isethionates in the cleansing composition is from about 5 to about 15 wt. %, preferably about 7 to about 14 wt. %, and more preferably about 8 to about 12 wt. %, based on the total weight of the cleansing composition.

Acyl Amino Acids

Acyl amino acids that may be used include, but are not limited to, amino acid surfactants based on alanine, arginine, aspartic acid, glutamic acid, glycine, isoleucine, leucine, lysine, phenylalanine, serine, tyrosine, valine, sarcosine, threonine, and taurine. The most common cation associated with the acyl amino acid can be sodium or potassium. Alternatively, the cation can be an organic salt such as triethanolamine (TEA) or a metal salt. Non-limiting examples of useful acyl amino acids include those of formula (III):

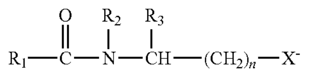

(III)

wherein R, $R^1$, $R^2$ and $R^3$ are each independently selected from H or an alkyl chain having 1-24 carbon atoms, said chain being saturated or unsaturated, linear or branched, and X is $COO^-$ or $SO_3^-$. In some embodiments, one or more acyl sarcosinates are preferred.

The total amount of the one or more acyl amino acids in the cleansing composition will vary but is typically from about 0.1 to about 10 wt. %, based on the total weight of the cleansing composition. in further embodiments, the cleansing composition include about 0.1 to about 8 wt. %, about 0.1 to about 5 wt. %, about 0.1 to about 3 wt. %, about 0.1 to about 2 wt. %, about 0.4 to about 10 wt. %, about 0.4 to about 8 wt. %, about 0.4 to about 5 wt. %, about 0.4 to about 3 wt. %, or about 0.4 to about 2 wt. % of the one or more acyl amino acids, based on the total weight of the cleansing composition. In a preferred embodiment, the cleansing compositions includes about 0.1 to about 10 wt. %, preferably about 0.2 to about 6 wt. %, and more preferably about 0.4 to about 4 wt. % of the one or more acyl amino acids, based on the total weight of the cleansing composition.

Acyl Sarcosinates

The cleansing composition may include one or more acyl sarcosinates. In various embodiments, the cleansing composition includes one or more acyl sarcosinates of formula (IV).

$$R—C(O)—N(CH_3)—CH_2—C(O)—OX \quad (IV)$$

wherein, X denotes a hydrogen atom, an ammonium ion, an ion derived from an alkali metal or an alkaline-earth metal or an ion derived from an organic amine, preferably a hydrogen atom.

R denotes a linear or branched alkyl group of 6 to 30 carbon atoms. Preferably, R denotes a linear or branched alkyl group of 8 to 24 carbon atoms, preferably of 12 to 20 carbon atoms.

Nonlimiting examples of specific acyl sarcosinates include potassium lauroyl sarcosinate, potassium cocoyl sarcosinate, sodium cocoyl sarcosinate, sodium lauroyl sarcosinate, sodium myristoyl sarcosinate, sodium oleoyl sarcosinate, sodium palmitoyl sarcosinate, and ammonium lauroyl sarcosinate. In some embodiments, sodium lauroyl sarcosinate is preferred.

The total amount of the one or more acyl sarcosinates in the cleansing composition, if present, may vary but is typically from about 0.1 to about 10 wt. %, based on the total weight of the cleansing composition. In some embodiments, the total amount of the one or more acyl sarcosinates in the cleansing composition, if present, is from about 0.1 to about 10 wt. %, about 0.1 to about 5 wt. %, about 0.1 to about 3 wt. %, about 0.5 to about 10 wt. %, about 0.5 to about 5 wt. %, about 0.5 to about 3 wt. %, about 1 to about 10 wt. %, about 1 to about 8 wt. %, about 1 to about 5 wt. %, about 1 to about 3 wt. %, about 2 to about 10 wt. %, about 2 to about 8 wt. %, or about 2 to about 5 wt. %, based on the total weight of the cleansing composition.

Acyl Taurates

Non-limiting examples of acyl taurates include those of formula (V):

(V)

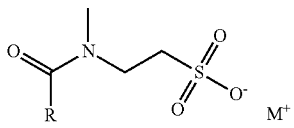

wherein R Is a linear or branched saturated alkyl group having from 6 to 30, preferably from 8 to 22, more preferably from 8 to 18, carbon atoms, or a linear or branched mono-or polyunsaturated alkenyl group having from 6 to 30, preferably from 8 to 22, more preferably from 12 to 18, carbon atoms, and $M^+$ is a cation. $M^+$ represents an optionally substituted ammonium cation or, most preferably, a metal cation. Suitable ammonium cations include $NH_4^+$ and the ammonium cation of triethanolamine. Suitable metal cations include alkali metal cations, for example sodium, lithium, and potassium cations, and alkaline earth metal cations, for example calcium and magnesium cations. Preferably $M^+$ represents a potassium or sodium cation.

Non-limiting examples of specific acyl taurate salts include sodium cocoyl taurate and sodium methyl cocoyl taurate.

The total amount of the one or more acyl taurates in the cleansing composition, if present, may vary but is typically from about 0.1 to about 10 wt. %, based on the total weight of the cleansing composition. In some embodiments, the total amount of the one or more acyl taurates in the cleansing composition, if present, is from about 0.1 to about 10 wt. %, about 0.1 to about 5 wt. %, about 0.1 to about 3 wt. %, about 0.5 to about 10 wt. %, about 0.5 to about 5 wt. %, about 0.5 to about 3 wt. %, about 1 to about 10 wt. %, about 1 to about 8 wt. %, about 1 to about 5 wt. %, about 1 to about 3 wt. %, about 2 to about 10 wt. %, about 2 to about 8 wt. %, or about 2 to about 5 wt. %, based on the total weight of the cleansing composition.

Acyl Glycinates

Non-limiting examples of useful acyl glycinates include those of formula (VI):

(VI)

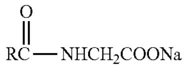

wherein R is an alkyl chain of 8 to 16 carbon atoms. Sodium is shown as the cation in the above formula (VI) but the cation may be an alkali metal ion such as sodium or potassium, ammonium ions, or alkanolammonium ions such as monoethanolammonium or triethanolammonium ions. Non-limiting examples of acyl glycinates include sodium cocoyl glycinate, sodium lauroyl glycinate, sodium myristoyl glycinate, potassium lauroyl glycinate, and potassium cocoyl glycinate, and in particular sodium cocoyl glycinate.

The total amount of the one or more acyl glycinates in the cleansing composition, if present, may vary but is typically from about 0.1 to about 10 wt. %, based on the total weight of the cleansing composition. In some embodiments, the total amount of the one or more acyl glycinates in the cleansing composition, if present, is from about 0.1 to about 10 wt. %, about 0.1 to about 5 wt. %, about 0.1 to about 3 wt. %, about 0.5 to about 10 wt. %, about 0.5 to about 5 wt. %, about 0.5 to about 3 wt. %, about 1 to about 10 wt. %, about 1 to about 8 wt. %, about 1 to about 5 wt. %, about 1 to about 3 wt. %, about 2 to about 10 wt. %, about 2 to about 8 wt. %, or about 2 to about 5 wt. %, based on the total weight of the cleansing composition.

Acyl Glutamates

Non-limiting examples of useful acyl glutamates include those of formula (VII):

(VII)

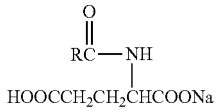

wherein R is an alkyl chain of 8 to 16 carbon atoms. Sodium is shown as the cation in the above formula (VII) but the cation may be an alkali metal ion such as sodium or potassium, ammonium ions, or alkanolammonium ions such as monoethanolammonium or triethanolammonium ions. Non-limiting examples of acyl glutamates include dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, sodium undecylenoyl glutamate, triethanolamine mono-cocoyl glutamate, triethanolamine lauroylglutamate, and disodium cocoyl glutamate. In some cases, sodium stearoyl glutamate is particularly preferred.

The total amount of the one or more acyl glutamates in the cleansing composition, if present, may vary but is typically from about 0.1 to about 10 wt. %, based on the total weight of the cleansing composition. In some embodiments, the total amount of the one or more acyl glutamates in the cleansing composition, if present, is from about 0.1 to about 10 wt. %, about 0.1 to about 5 wt. %, about 0.1 to about 3 wt. %, about 0.5 to about 10 wt. %, about 0.5 to about 5 wt. %, about 0.5 to about 3 wt. %, about 1 to about 10 wt. %, about 1 to about 8 wt. %, about 1 to about 5 wt. %, about 1 to about 3 wt. %, about 2 to about 10 wt. %, about 2 to about 8 wt. %, or about 2 to about 5 wt. %, based on the total weight of the cleansing composition.

Alkyl Sulfonates

Nonlimiting examples of alkyl sulfonates include alkyl aryl sulfonates, primary alkane disulfonates, alkene sulfonates, hydroxyalkane sulfonates, alkyl glyceryl ether sulfonates, alpha-olefinsulfonates, sulfonates of alkylphenolpolyglycol ethers, alkylbenzenesulfonates, phenylalkanesulfonates, alpha-olefinsulfonates, olefin sulfonates, alkene sulfonates, hydroxyalkanesulfonates and disulfonates, secondary alkanesulfonates, paraffin sulfonates, ester sulfonates, sulfonated fatty acid glycerol esters, and alpha-sulfo fatty acid methyl esters including methyl ester sulfonate.

In some embodiments, an alkyl sulfonate of formula (VIII) is particularly useful.

(VIII)

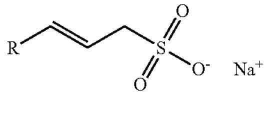

R is selected from H or alkyl chain that has 1-24 carbon atoms, preferably 6-24 carbon atoms, and more preferably 8 to 20 carbon atoms, said chain being saturated or unsaturated, linear or branched. Sodium is shown as the cation in the above formula (III) but the cation may be an alkali metal ion such as sodium or potassium, ammonium ions, or alkanolammonium ions such as monoethanolammonium or triethanolammonium ions. In some embodiments, the alkyl sulfonate(s) are selected from $C_8$-$C_{16}$ alkyl benzene sulfonates, $C_{10}$-$C_{20}$ paraffin sulfonates, $C_{10}$-$C_{24}$ olefin sulfonates, salts thereof, and combinations thereof. $C_{10}$-$C_{24}$ olefin sulfonates are particularly preferred. A non-limiting but particularly useful example of a $C_{10}$-$C_{24}$ olefin sulfonate that can be used in the instant compositions is sodium $C_{14-16}$ olefin sulfonate.

The total amount of the one or more alkyl sulfonates in the cleansing composition, if present, may vary but is typically from about 0.1 to about 10 wt. %, based on the total weight of the cleansing composition. In some embodiments, the total amount of the one or more alkyl sulfonates in the cleansing composition, if present, is from about 0.1 to about 10 wt. %, about 0.1 to about 5 wt. %, about 0.1 to about 3 wt. %, about 0.5 to about 10 wt. %, about 0.5 to about 5 wt. %, about 0.5 to about 3 wt. %, about 1 to about 10 wt. %, about 1 to about 8 wt. %, about 1 to about 5 wt. %, about 1 to about 3 wt. %, about 2 to about 10 wt. %, about 2 to about 8 wt. %, or about 2 to about 5 wt. %, based on the total weight of the cleansing composition.

Alkyl Sulfosuccinates

Non-limiting examples of useful alkyl sulfosuccinates include those of formula (IX):

(IX)

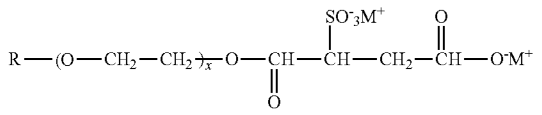

wherein R is a straight or branched chain alkyl or alkenyl group having 10 to 22 carbon atoms, preferably 10 to 20 carbon atoms, x is a number that represents the average degree of ethoxylation and can range from 0 to about 5, preferably from 0 to about 4, and most preferably from about 2 to about 3.5, and M is a monovalent cation which can be the same or different from each other. Preferred cations are alkali metal ions such as sodium or potassium, ammonium ions, or alkanolammonium ions such as monoethanolammonium or triethanolammonium ions.

Non-limiting examples of alkyl sulfosuccinates salts include disodium oleamido MIPA sulfosuccinate, disodium oleamido MEA sulfosuccinate, disodium lauryl sulfosuccinate, disodium laureth sulfosuccinate, diammonium lauryl sulfosuccinate, diammonium laureth sulfosuccinate, dioctyl sodium sulfosuccinate, disodium oleamide MEA sulfosuccinate, sodium dialkyl sulfosuccinate, and a combination thereof. In some embodiments, disodium laureth sulfosuccinate is particularly preferred.

The total amount of the one or more alkyl sulfosuccinates in the cleansing composition, if present, may vary but is typically from about 0.1 to about 10 wt. %, based on the total weight of the cleansing composition. In some embodiments, the total amount of the one or more alkyl sulfosuccinates in the cleansing composition, if present, is from about 0.1 to about 10 wt. %, about 0.1 to about 5 wt. %, about 0.1 to about 3 wt. %, about 0.5 to about 10 wt. %, about 0.5 to about 5 wt. %, about 0.5 to about 3 wt. %, about 1 to about 10 wt. %, about 1 to about 8 wt. %, about 1 to about 5 wt. %, about 1 to about 3 wt. %, about 2 to about 10 wt. %, about 2 to about 8 wt. %, or about 2 to about 5 wt. %, based on the total weight of the cleansing composition.

Alkyl Sulfoacetates

Non-limiting examples of alkyl sulfoacetates include, for example, alkyl sulfoacetates such as C4-C18 fatty alcohol sulfoacetates and/or salts thereof. A particularly preferred sulfoacetate salt is sodium lauryl sulfoacetate. Useful cations for the salts include alkali metal ions such as sodium or potassium, ammonium ions, or alkanolammonium ions such as monoethanolammonium or triethanolammonium ions.

The total amount of the one or more alkyl sulfoacetates in the cleansing composition, if present, may vary but is typically from about 0.1 to about 10 wt. %, based on the total weight of the cleansing composition. In some embodiments, the total amount of the one or more alkyl sulfoacetates in the cleansing composition, if present, is from about 0.1 to about 10 wt. %, about 0.1 to about 5 wt. %, about 0.1 to about 3 wt. %, about 0.5 to about 10 wt. %, about 0.5 to about 5 wt. %, about 0.5 to about 3 wt. %, about 1 to about 10 wt. %, about 1 to about 8 wt. %, about 1 to about 5 wt. %, about 1 to about 3 wt. %, about 2 to about 10 wt. %, about 2 to about 8 wt. %, or about 2 to about 5 wt. %, based on the total weight of the cleansing composition.

Alkoxylated Monoacids

Non-limiting examples of alkoxylated monoacids include compounds corresponding to formula (X):

$$RO[CH_2O]_u[(CH_2)_xCH(R')(CH_2)_y(CH_2)_zO]_v[CH_2CH_2O]_wCH_2COOH \quad (X)$$

wherein:

R is a hydrocarbon radical containing from about 6 to about 40 carbon atoms;

u, v and w, independently of one another, represent numbers of from 0 to 60;

x, y and z, independently of one another, represent numbers of from 0 to 13;

R' represents hydrogen or alkyl containing from about 1 to about 20 carbon atoms, and the sum of x+y+z>0;

Compounds corresponding to formula (X) can be obtained by alkoxylation of alcohols ROH with ethylene oxide as the sole alkoxide or with several alkoxides and subsequent oxidation. The numbers u, v, and w each represent the degree of alkoxylation. Whereas, on a molecular level, the numbers u, v and w and the total degree of alkoxylation can only be integers (including zero), but on a macroscopic level, they are mean values in the form of broken numbers.

In formula (X), R is linear or branched, acyclic or cyclic, saturated or unsaturated, aliphatic or aromatic, substituted or unsubstituted. Typically, R is a linear or branched, acyclic C6-40 alkyl or alkenyl group or a C1-40 alkyl phenyl group, more typically a C8-22 alkyl or alkenyl group or a C4-18 alkyl phenyl group, and even more typically a C12-18 alkyl group or alkenyl group or a C6-16 alkyl phenyl group; u, v, w, independently of one another, is typically a number from 2 to 20, more typically a number from 3 to 17 and most typically a number from 5 to 15; x, y, z, independently of one another, is typically a number from 2 to 13, more typically a number from 1 to 10 and most typically a number from 0 to 8.

Suitable alkoxylated monoacids include, but are not limited to: Butoxynol-5 Carboxylic Acid, Butoxynol-19 Carboxylic Acid, Capryleth-4 Carboxylic Acid, Capryleth-6

Carboxylic Acid, Capryleth-9 Carboxylic Acid, Ceteareth-25 Carboxylic Acid, Coceth-7 Carboxylic Acid, C9-11 Pareth-6 Carboxylic Acid, C11-15 Pareth-7 Carboxylic Acid, C12-13 Pareth-5 Carboxylic Acid, C12-13 Pareth-8 Carboxylic Acid, C12-13 Pareth-12 Carboxylic Acid, C12-15 Pareth-7 Carboxylic Acid, C12-15 Pareth-8 Carboxylic Acid, C14-15 Pareth-8 Carboxylic Acid, Deceth-7 Carboxylic Acid, Laureth-3 Carboxylic Acid, Laureth-4 Carboxylic Acid, Laureth-5 Carboxylic Acid, Laureth-6 Carboxylic Acid, Laureth-8 Carboxylic Acid, Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid, PPG-6-Laureth-6 Carboxylic Acid, PPG-8-Steareth-7 Carboxylic Acid, Myreth-3 Carboxylic Acid, Myreth-5 Carboxylic Acid, Nonoxynol-5 Carboxylic Acid, Nonoxynol-8 Carboxylic Acid, Nonoxynol-10 Carboxylic Acid, Octeth-3 Carboxylic Acid, Octoxynol-20 Carboxylic Acid, Oleth-3 Carboxylic Acid, Oleth-6 Carboxylic Acid, Oleth-10 Carboxylic Acid, PPG-3-Deceth-2 Carboxylic Acid, Capryleth-2 Carboxylic Acid, Ceteth-13 Carboxylic Acid, Deceth-2 Carboxylic Acid, Hexeth-4 Carboxylic Acid, Isosteareth-6 Carboxylic Acid, Isosteareth-11 Carboxylic Acid, Trudeceth-3 Carboxylic Acid, Trideceth-6 Carboxylic Acid, Trideceth-8 Carboxylic Acid, Trideceth-12 Carboxylic Acid, Trideceth-3 Carboxylic Acid, Trideceth-4 Carboxylic Acid, Trideceth-7 Carboxylic Acid, Trideceth-15 Carboxylic Acid, Trideceth-19 Carboxylic Acid, Undeceth-5 Carboxylic Acid and combinations thereof. In some cases, preferred ethoxylated acids include Oleth-10 Carboxylic Acid, Laureth-5 Carboxylic Acid, Laureth-11 Carboxylic Acid, and a combination thereof.

The total amount of the one or more alkoxylated monoacids in the cleansing composition, if present, may vary but is typically from about 0.1 to about 10 wt. %, based on the total weight of the cleansing composition. In some embodiments, the total amount of the one or more alkoxylated monoacids in the cleansing composition, if present, is from about 0.1 to about 10 wt. %, about 0.1 to about 5 wt. %, about 0.1 to about 3 wt. %, about 0.5 to about 10 wt. %, about 0.5 to about 5 wt. %, about 0.5 to about 3 wt. %, about 1 to about 10 wt. %, about 1 to about 8 wt. %, about 1 to about 5 wt. %, about 1 to about 3 wt. %, about 2 to about 10 wt. %, about 2 to about 8 wt. %, or about 2 to about 5 wt. %, based on the total weight of the cleansing composition.

Additional Non-Sulfate-Based Anionic Surfactants

Nonlimiting examples of additional non-sulfate-based anionic surfactants include saponified oils and neutralized fatty acids. For example, the non-sulfate-based anionic surfactant may be selected from one or more salts of $C_8$-$C_{22}$ saturated or unsaturated fatty acids, such as one or more of sodium cocoate, sodium tallowate, sodium laurate, sodium myristate, sodium stearate, sodium palmate, sodium palm kernelate, sodium olivate, potassium cocoate, potassium tallowate, potassium laurate, potassium myristate, potassium stearate, potassium palmate, potassium palm kernelate, potassium olivate, mono-, di- or tri-ethanolamine cocoate, mono-, di- or tri-ethanolamine tallowate, mono-, di- or tri-ethanolamine laurate, mono-, di- or tri-ethanolamine myristate, mono-, di- or tri-ethanolamine stearate, mono-, di- or tri-ethanolamine palmate, mono-, di- or tri-ethanolamine palm kernelate, and mono-, di- or tri-ethanolamine olivate. In a preferred embodiment, the cleansing composition includes at least one non-sulfate-based anionic surfactant selected from sodium cocoate, sodium tallowate, sodium laurate, sodium myristate, sodium stearate, sodium palmate, sodium palm kernelate, and sodium olivate. In a particularly preferred embodiment, the cleansing composition includes a cocoate, for example, a cocoate selected from sodium cocoate, potassium cocoate, mono-, di- or tri-ethanolamine cocoate, or a combination thereof.

The total amount of the one or more additional non-sulfate-based anionic surfactants in the cleansing composition, if present, may vary but is typically from about 0.0.05 to about 10 wt. %, based on the total weight of the cleansing composition. In some embodiments, the total amount of the one or more additional non-sulfate-based anionic surfactants in the cleansing composition, if present, is from about 0.1 to about 10 wt. %, about 0.1 to about 5 wt. %, about 0.1 to about 3 wt. %, about 0.1 to about 1 wt. %, about 0.2 to about 5 wt. %, about 0.2 to about 3 wt. %, or about 0.2 to about 1 wt. %, based on the total weight of the cleansing composition.

(b) Amphoteric Surfactants

Nonlimiting examples of amphoteric surfactants include alkyl amphoproprionates, betaines, alkyl sultaines, alkyl amphoacetates, and combinations thereof. Preferably, at least one of the one or more amphoteric surfactants is a betaine.

The total amount of the one or more amphoteric surfactants in the cleansing compositions will vary but is typically from about 0.1 to about 15 wt. %, based on the total weight of the cleansing composition. In some embodiments, the total amount of the one or more amphoteric surfactants in the cleansing composition is from about 0.1 to about 10 wt. %, from about 0.1 to about 8 wt. %, about 0.1 to about 5 wt. %, about 0.1 to about 3 wt. %, about 1 to about 15 wt. %, about 1 to about 10 wt. %, about 1 to about 8 wt. %, about 1 to about 5 wt. %, about 1 to about 3 wt. %, about 2 to about 15 wt. %, about 2 to about 10 wt. %, or about 2 to about 8 wt. %, about 2 to about 5 wt. %, or about 2 to about 4 wt. %, based on the total weight of the cleansing composition.

Alkyl Amphopropionates

In some embodiments, the cleansing compositions preferably include one or more alkyl amphopropionates. Nonlimiting examples of alkyl amphopropionates include cocoamphopropionate, cornamphopropionate, caprylamphopropionate, cornamphopropionate, caproamphopropionate, oleoamphopropionate, isostearoamphopropionate, stearoamphopropionate, lauroamphopropionate, salts thereof, and a combination thereof. Sodium cocoamphopropionate is a particularly useful alkyl amphopropionate that can be included in the cleansing compositions.

The total amount of the one or more alkyl amphopropionates in the cleansing composition, if present, may vary but is typically from about 0.01 to about 15 wt. %, based on the total weight of the cleansing composition. In some embodiments, the total amount of the one or more amphopropionates in the cleansing composition is from about 0.01 to about 10 wt. %, about 0.01 to about 5 wt. %, about 0.1 to about 15 wt. %, or about 0.1 to about 10 wt. %, about 0.1 to about 5 wt. %, about 0.1 to about 3 wt. %, about 1 to about 15 wt. %, about 1 to about 10 wt. %, about 1 to about 5 wt. %, or about 1 to about 3 wt. % based on the total weight of the cleansing composition.

Betaines

Useful betaines include those of the following formulae (XIa-XId):

(XIa)

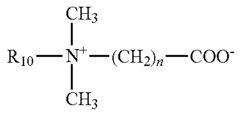

-continued (XIb)

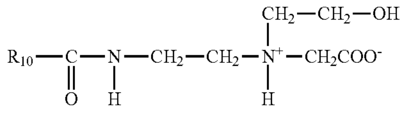

(XIc)

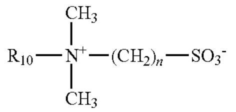

(XId)

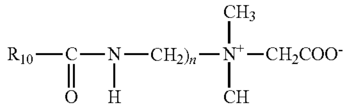

wherein $R_{10}$ is an alkyl group having 8-18 carbon atoms; and n is an integer from 1 to 3.

Particularly useful betaines include, for example, coco betaine, cocamidopropyl betaine, lauryl betaine, laurylhydroxy sulfobetaine, lauryldimethyl betaine, cocamidopropyl hydroxysultaine, behenyl betaine, capryl/capramidopropyl betaine, lauryl hydroxysultaine, stearyl betaine, and combinations thereof. Typically, at least one betaine compound is selected from coco betaine, cocamidopropyl betaine, behenyl betaine, capryl/capramidopropyl betaine, and lauryl betaine, and combinations thereof. Particularly preferred betaines include coco betaine and cocamidopropyl betaine.

In a preferred embodiment, the cleansing composition includes at least one betaine, preferably at least two betaines.

The total amount of the one or more betaines in the cleansing composition, if present, may vary but is typically from about 0.01 to about 15 wt. %, based on the total weight of the cleansing composition. In some embodiments, the total amount of the one or more betaines in the cleansing composition is from about 0.01 to about 10 wt. %, about 0.01 to about 5 wt. %, about 0.1 to about 15 wt. %, or about 0.1 to about 10 wt. %, about 0.1 to about 5 wt. %, about 0.1 to about 3 wt. %, about 1 to about 15 wt. %, about 1 to about 10 wt. %, about 1 to about 5 wt. %, or about 1 to about 3 wt. % based on the total weight of the cleansing composition.

Alkyl Sultaines

Non-limiting examples of alkyl sultaines include hydroxyl sultaines of formula (XII)

(XII)

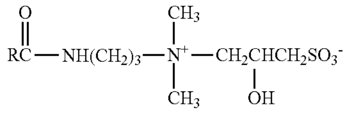

wherein R is an alkyl group having 8-18 carbon atoms. More specific examples include, but are not limited to cocamidopropyl hydroxysultaine, lauryl hydroxysultaine, and a combination thereof.

The total amount of the one or more alkyl sultaines in the cleansing composition, if present, may vary but is typically from about 0.01 to about 15 wt. %, based on the total weight of the cleansing composition. In some embodiments, the total amount of the one or more alkyl sultaines in the cleansing composition is from about 0.01 to about 10 wt. %, about 0.01 to about 5 wt. %, about 0.1 to about 15 wt. %, or about 0.1 to about 10 wt. %, about 0.1 to about 5 wt. %, about 0.1 to about 3 wt. %, about 1 to about 15 wt. %, about 1 to about 10 wt. %, about 1 to about 5 wt. %, or about 1 to about 3 wt. % based on the total weight of the cleansing composition.

Alkyl Amphoacetates and Alkyl Amphodiacetates

Useful alkyl amphoacetates and alkyl amphodiacetates include those of Formulae (XIII) and (XIV), respectively:

(XIII)

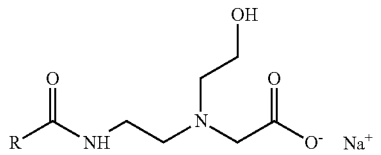

(XIV)

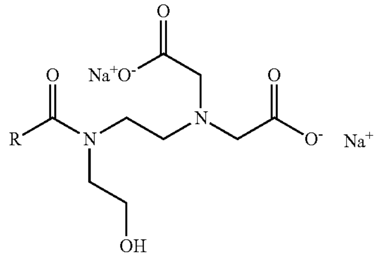

wherein R is an alkyl group having 8-18 carbon atoms. Sodium is shown as the cation in the formulae above, but the cation may be an alkali metal ion such as sodium or potassium, ammonium ions, or alkanolammonium ions such as monoethanolammonium or triethanolammonium ions. A more specific, but non-limiting example, is sodium lauroamphoacetate.

The total amount of the one or more alkyl amphoacetates and/or alkyl amphodiacetates in the cleansing composition, if present, may vary but is typically from about 0.01 to about 15 wt. %, based on the total weight of the cleansing composition. In some embodiments, the total amount of the one or more alkyl amphoacetates and/or alkyl amphodiacetates in the cleansing composition is from about 0.01 to about 10 wt. %, about 0.01 to about 5 wt. %, about 0.1 to about 15 wt. %, or about 0.1 to about 10 wt. %, about 0.1 to about 5 wt. %, about 0.1 to about 3 wt. %, about 1 to about 15 wt. %, about 1 to about 10 wt. %, about 1 to about 5 wt. %, or about 1 to about 3 wt. % based on the total weight of the cleansing composition.

(c) Nonionic Surfactants

The cleansing compositions include one or more nonionic surfactants, preferably a plurality of nonionic surfactants. Non-limiting examples of nonionic surfactants include: alkyl polyglucosides; alkanolamides; polyoxyalkylenated nonionic surfactants; polyglycerolated nonionic surfactants; ethoxylated fatty esters; alcohols, alpha-diols, alkylphenols and esters of fatty acids, being ethoxylated, propoxylated, or glycerolated; copolymers of ethylene oxide and/or of propylene oxide; condensates of ethylene oxide and/or of propylene oxide with fatty alcohols; polyethoxylated fatty amides; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives, amine oxides such as ($C_{10}$-$C_{14}$)alkylamine oxides or N—($C_{10}$-$C_{14}$)acylaminopropylmorpholine oxides; and combinations thereof. The cleansing composition preferably includes a plurality of nonionic surfactants, wherein the plurality of nonionic surfactants includes one or more polyglucosides and one or more additional nonionic surfactants, preferably selected from PEGylated nonionic surfactants, more preferably selected from PEG-55 propylene glycol oleate, PEG-150 distearate, PPG-5-Ceteth-20, or a combination thereof.

The total amount of the one or more nonionic surfactants in the cleansing composition may vary but is typically about 0.1 to about 20 wt. %, based on the total weight of the cleansing composition. In some embodiments, the total amount of the one or more nonionic surfactants is about 0.1 to about 15 wt. % about 0.1 to about 12 wt. %, about 0.1 to about 10 wt. %, about 0.1 to about 8 wt. %, about 0.1 to about 5 wt. %, about 1 to about 20 wt. %, about 1 to about 15 wt. %, about 1 to about 12 wt. %, about 1 to about 8 wt. %, about 1 to about 5 wt. %, about 2 to about 20 wt. %, about 2 to about 15 wt. %, about 2 to about 12 wt. %, about 2 to about 8 wt. %, about 2 to about 5 wt. %, about 5 to about 20 wt. %, about 5 to about 15 wt. %, about 5 to about 12 wt. %, about 5 to about 10 wt. %, about 8 to about 20 wt. %, about 8 to about 15 wt. %, or about 8 to about 12 wt. %, based on a total weight of the cleansing composition.

In a preferred embodiment, the cleansing composition includes about 1 to about 20 wt. %, preferably about 5 to about 15 wt. %, more preferably about 8 to about 12 wt. % of the one or more nonionic surfactants, based on the total weight of the cleansing composition.

Alkyl Polyglucosides

Useful alkyl polyglucosides include those having the following formula (XV):

$$R^1—O—(R^2O)_n—Z(x) \quad (XV)$$

wherein $R^1$ is an alkyl group having 8-18 carbon atoms;

$R^2$ is an ethylene or propylene group;

Z is a saccharide group with 5 to 6 carbon atoms;

n is an integer from 0 to 10; and x is an integer from 1 to 5.

Useful alkyl polyglucosides include lauryl glucoside, octyl glucoside, decyl glucoside, coco glucoside, caprylyl/capryl glucoside, and sodium lauryl glucose carboxylate. Typically, the at least one alkyl poly glucoside compound is selected from the group consisting of lauryl glucoside, decyl glucoside and coco glucoside. In some embodiments, decyl glucoside is particularly preferred.

The total amount of the one or more alkyl polyglucosides in the cleansing composition, if present, may vary but is typically about 0.1 to about 20 wt. %, based on the total weight of the cleansing composition. In some embodiments, the total amount of the one or more alkyl polyglucosides is about 0.1 to about 15 wt. %, about 0.1 to about 12 wt. %, about 0.1 to about 10 wt. %, about 0.1 to about 8 wt. %, about 0.1 to about 5 wt. %, about 1 to about 20 wt. %, about 1 to about 15 wt. %, about 1 to about 12 wt. %, about 1 to about 8 wt. %, about 1 to about 5 wt. %, about 2 to about 20 wt. %, about 2 to about 15 wt. %, about 2 to about 12 wt. %, about 2 to about 8 wt. %, about 2 to about 5 wt. %, about 5 to about 20 wt. %, about 5 to about 15 wt. %, about 5 to about 12 wt. %, about 5 to about 10 wt. %, about 8 to about 20 wt. %, about 8 to about 15 wt. %, or about 8 to about 12 wt. %, based on a total weight of the cleansing composition.

In a preferred embodiment, the cleansing composition includes about 1 to about 20 wt. %, preferably about 5 to about 15 wt. %, and more preferably about 6 to about 12 wt. % of the one or more alkyl polyglucosides, based on the total weight of the cleansing composition.

Alkanolamides

Non-limiting examples of alkanolamides include fatty acid alkanolamides. The fatty acid alkanolamides may be fatty acid monoalkanolamides, fatty acid dialkanolamides, or fatty acid isoalkanolamides, and may have a $C_{2-8}$ hydroxyalkyl group (the $C_{2-8}$ chain can be substituted with one or more than one —OH group). Non-limiting examples include fatty acid diethanolamides (DEA) or fatty acid monoethanolamides (MEA), fatty acid monoisopropanolamides (MIPA), fatty acid diisopropanolamides (DIPA), and fatty acid glucamides (acyl glucamides).

Suitable fatty acid alkanolamides include those formed by reacting an alkanolamine and a C6-C36 fatty acid. Examples include, but are not limited to: oleic acid diethanolamide, myristic acid monoethanolamide, soya fatty acids diethanolamide, stearic acid ethanolamide, oleic acid monoisopropanolamide, linoleic acid diethanolamide, stearic acid monoethanolamide (Stearamide MEA), behenic acid monoethanolamide, isostearic acid monoisopropanolamide (isostearamide MIPA), erucic acid diethanolamide, ricinoleic acid monoethanolamide, coconut fatty acid monoisopropanolamide (cocoamide MIPA), coconut acid monoethanolamide (Cocamide MEA), palm kernel fatty acid diethanolamide, coconut fatty acid diethanolamide, lauric diethanolamide, polyoxyethylene coconut fatty acid monoethanolamide, coconut fatty acid monoethanolamide, lauric monoethanolamide, lauric acid monoisopropanolamide (lauramide MIPA), myristic acid monoisopropanolamide (Myristamide MIPA), coconut fatty acid diisopropanolamide (cocamide DIPA), and combinations thereof.

In some embodiments, the fatty acid alkanolamides preferably include cocamide MIPA, cocamide DEA, cocamide MEA, cocamide DIPA, and combinations thereof. In particular, the fatty acid alkanolamide may be cocamide MIPA, which is commercially available under the tradename "EMPILAN" from Innospec Active Chemicals.

Fatty acid alkanolamides include those having the following formula (XVI):

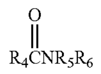

(XVI)

wherein $R_4$ is an alkyl chain of 4 to 20 carbon atoms ($R_4$ may be, for example, selected from lauric acid, coconut acid, palmitic acid, myristic acid, behenic acid, babassu fatty acid, isostearic acid, stearic acid, corn fatty acid, soy fatty acid, shea butter fatty acids, caprylic acid, capric acid, and combinations thereof);

$R_5$ is selected from $—CH_2OH$, $—CH_2CH_2OH$, $—CH_2CH_2CH_2OH$, $—CH_2(CHOH)_4CH_2OH$, -benzyl, and combinations thereof; and $R_6$ is selected from —H, $—CH_3$, $—CH_2OH$, $—CH_2CH_3$, $—CH_2CH_2OH$, $—CH_2CH_2CH_2OH$, $—CH_2(CHOH)_4CH_2OH$, -benzyl, and combinations thereof.

In some embodiments, the one or more of the fatty acid alkanolamides include one or more acyl glucamides, for example, acyl glucamides having a carbon chain length of 8 to 20. Non-limiting examples include lauroyl/myristoyl methyl glucamide, capryloyl/capryl methyl glucamide, lauroyl methyl glucamide, myristoyl methyl glucamide, capryloyl methyl glucamide, capryl methyl glucamide, cocoyl methyl glucamide, capryloyl/caproyl methyl glucamide, cocoyl methyl glucamide, lauryl methylglucamide, oleoyl methylglucamide oleate, stearoyl methylglucamide stearate, sunfloweroyl methylglucamide, and tocopheryl succinate methylglucamide.

The total amount of one or more alkanolamides in the cleansing compositions, if present, can vary but is typically about 0.1 to about 15 wt. %, based on the total weight of the cleansing composition. In some instances, the total amount of the one or more alkanolamides is about 0.1 to about 10 wt. %, about 0.1 to about 8 wt. %, about 0.1 to about 5 wt. %, about 0.1 to about 3 wt. %, about 0.5 to about 15 wt. %, about 0.5 to about 12 wt. %, about 0.5 to about 10 wt. %, about 0.5 to about 8 wt. %, about 0.5 to about 5 wt. %, based on a total weight of the cleansing composition.

Additional Nonionic Surfactants

Nonionic surfactants also include, for example, alcohols, alpha-diols, alkylphenols and esters of fatty acids, being ethoxylated, propoxylated or glycerolated and having at least one fatty chain comprising, for example, from 8 to 18 carbon atoms, it being possible for the number of ethylene oxide or propylene oxide groups to range from 2 to 50, and for the number of glycerol groups to range from 1 to 30. Maltose derivatives may also be mentioned. Non-limiting mention may also be made of copolymers of ethylene oxide and/or of propylene oxide; condensates of ethylene oxide and/or of propylene oxide with fatty alcohols; polyethoxylated fatty amides comprising, for example, from 2 to 30 mol of ethylene oxide; polyglycerolated fatty amides comprising, for example, from 1.5 to 5 glycerol groups, such as from 1.5 to 4; ethoxylated fatty acid esters of sorbitan comprising from 2 to 30 mol of ethylene oxide; ethoxylated oils from plant origin; fatty acid esters of sucrose; fatty acid esters of polyethylene glycol; polyethoxylated fatty acid mono or diesters of glycerol ($C_6$-$C_{24}$)alkylpolyglycosides; N—($C_6$-$C_{24}$)alkylglucamine derivatives; amine oxides such as ($C_{10}$-$C_{14}$)alkylamine oxides or N—($C_{10}$-$C_{14}$)acylaminopropylmorpholine oxides; and combinations thereof.

Such nonionic surfactants may preferably be chosen from polyoxyalkylenated or polyglycerolated (alkoxylated) nonionic surfactants, polyoxyalkylenated or polyglycerolated (alkoxylated) propylene glycol oleate, or a combination thereof. The oxyalkylene units are more particularly oxyethylene or oxypropylene units, or a combination thereof, and are preferably oxyethylene units. A nonlimiting example of an alkoxylated (PEGylated) propylene glycol oleate is PEG-55 propylene glycol oleate.

In some cases, the nonionic surfactant may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and combinations thereof.

Examples of ethoxylated fatty esters that may be mentioned include the adducts of ethylene oxide with esters of lauric acid, palmitic acid, stearic acid or behenic acid, and combinations thereof, especially those containing from 9 to 100 oxyethylene groups, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and combinations thereof.

As glyceryl esters of fatty acids, glyceryl stearate (glyceryl mono-, di- and/or tristearate) (CTFA name: glyceryl stearate) or glyceryl ricinoleate and combinations thereof can in particular be used. As glyceryl esters of $C_8$-$C_{24}$ alkoxylated fatty acids, polyethoxylated glyceryl stearate (glyceryl mono-, di- and/or tristearate) such as PEG-20 glyceryl stearate can for example be used.

The total amount of the one or more additional nonionic surfactants in the cleansing compositions, if present, will vary but is typically from about 0.1 to about 15 wt. %, based on the total weight of the cleansing composition. In some embodiments, the total amount of the one or more additional nonionic surfactants is about 0.1 to about 10 wt. %, about 0.1 to about 8 wt. %, about 0.1 to about 5 wt. %, about 0.1 to about 3 wt. %, about 0.5 to about 15 wt. %, about 0.5 to about 12 wt. %, about 0.5 to about 10 wt. %, about 0.5 to about 8 wt. %, about 0.5 to about 5 wt. %, about 0.5 to about 3 wt. %, or about 0.3 to about 2 wt. %, based on a total weight of the cleansing composition.

Total Amount of Surfactants ((a), (b), and (c))

The total amount of the: (a) one or more anionic surfactants, (b) one or more amphoteric surfactants, and (c) the one or more nonionic surfactants will vary but is typically from about 15 to about 40 wt. %, based on the total weight of the cleansing composition. In further embodiments, the total amount of (a), (b), and (c) is from about 15 to about 35 wt. %, about 15 to about 30 wt. %, about 15 to about 25 wt. %, about 18 to about 40 wt. %, about 18 to about 35 wt. %, about 18 to about 30 wt. %, about 18 to about 25 wt. %, about 20 to about 40 wt. %, about 20 to about 35 wt. %, about 20 to about 30 wt. %, or about 20 to about 25 wt. %, based on the total weight of the cleansing composition. In a preferred embodiment, the cleansing composition includes about 15 to about 40 wt. %, preferably about 16 to about 30 wt. %, more preferably about 18 to about 28 wt. %, and even more preferably about 20 to about 26 wt. % of (a), (b), and (c).

Cationic surfactants are not typically used in cleansing compositions generally and are preferably not included in the cleansing compositions of the instant disclosure, at least not in an appreciable amount. In various embodiments, the cleansing composition is free or essentially free from cationic surfactants. In further embodiments, the cleansing composition includes less than 5 wt. %, preferably less than 2 wt. %, more preferably less than 1 wt. %, and even more preferably less than 0.5 wt. % of cationic surfactants. In a preferred embodiment, the cleansing composition includes less than 0.1 wt. % of one or more cationic surfactants.

(d) Hydroxypropyl Guar Hydroxypropyltrimonium Chloride

The total amount of the hydroxypropyl guar hydroxypropyltrimonium chloride in the cleansing composition will vary but is typically from about 0.1 to about 5 wt. %, based on the total weight of the cleansing composition. In further embodiments, the cleansing composition includes about 0.1 to about 3 wt. %, about 0.1 to about 2 wt. %, about 0.1 to about 1 wt. %, about 0.3 to about 5 wt. %, about 0.3 to about 3 wt. %, about 0.3 to about 2 wt. %, or about 0.3 to about 1 wt. % of the hydroxypropyl guar hydroxypropyltrimonium chloride, based on the total weight of the cleansing composition. In a preferred embodiment, the cleansing composition includes from about 0.1 to about 5 wt. %, preferably from about 0.2 to about 3 wt. %, and more preferably about 0.3 to about 2 wt. % of the hydroxypropyl guar hydroxypropyltrimonium chloride, based on the total weight of the cleansing composition.

(e) Cationic Polymers Other than a Cationic Guar

The cationic polymers may be homopolymers or formed from two or more types of monomers. The molecular weight of the cationic polymers may be between 5,000 and 10,000,000, typically at least 10,000, and preferably in the range 100,000 to about 2,000,000. These cationic polymers will typically have cationic nitrogen containing groups such as quaternary ammonium or protonated amino groups, or a combination thereof.

The cationic charge density is suitably at least 0.1 meq/g, preferably above 0.8 or higher. In some embodiments, the cationic charge density does not exceed 3 meq/g, or does not exceed 2 meq/g. The charge density can be measured using the Kjeldahl method and can be within the above limits at the desired pH of use, which will in general be from about 3 to 9 and preferably between 4 and 8.

The cationic nitrogen-containing group will generally be present as a substituent on a fraction of the total monomer units of the cationic polymer. Thus, when the polymer is not a homopolymer, it can contain spacer non-cationic monomer units.

Suitable cationic polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have $C_1$-$C_7$ alkyl groups, more preferably $C_1$-$C_3$ alkyl groups. Other suitable spacers include vinyl esters, vinyl alcohol, maleic anhydride, propylene glycol and ethylene glycol.

The cationic amines can be primary, secondary, or tertiary amines, depending upon the particular species and the pH of the composition.

Amine substituted vinyl monomers and amines can be polymerized in the amine form and then converted to ammonium by quaternization.

Suitable cationic amino and quaternary ammonium monomers include, for example, vinyl compounds substituted with dialkyl aminoalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidine, e.g., alkyl vinyl imidazolium, and quaternized pyrrolidine, e.g., alkyl vinyl imidazolium, alkyl vinyl pyridinium, alkyl vinyl pyrrolidine salts. The alkyl portions of these monomers are preferably lower alkyls such as the $C_1$-$C_3$ alkyls, more preferably $C_1$ and $C_2$ alkyls.

Suitable amine-substituted vinyl monomers include dialkylaminoalkyl acrylate, dialkylaminoalkyl methacrylate, dialkylaminoalkyl acrylamide, and dialkylaminoalkyl methacrylamide, wherein the alkyl groups are preferably $C_1$-$C_7$ hydrocarbyls, more preferably $C_1$-$C_3$ alkyls.

The cationic polymers can comprise mixtures of monomer units derived from amine- and/or quaternary ammonium-substituted monomer and/or compatible spacer monomers.

Suitable cationic polymers include, for example: copolymers of 1-vinyl-2-pyrrolidine and 1-vinyl-3-methyl-imidazolium salt (e.g., Chloride salt) (referred to as Polyquaternium-16) such as those commercially available from BASF under the "LUVIQUAT" tradename (e.g., "LUVIQUAT FC 370"); copolymers of 1-vinyl-2-pyrrolidine and dimethylaminoethyl methacrylate (referred to as "Polyquaternium-11") such as those commercially from Gar Corporation (Wayne, N.J., USA) under the "GAFQUAT" tradename (e.g., "GAFQUAT 755N"); cationic diallyl quaternary ammonium-containing polymer including, for example, dimethyldiallyammonium chloride homopolymer and copolymers of acrylamide and dimethyldiallyammonium chloride (referred to as "Polyquaternium-6" and "Polyquaternium-7"); and combinations thereof.

Polyquaterniums include Polyquaternium-1 (ethanol, 2,2',2''-nitrilotris-, polymer with 1,4-dichloro-2-butene and N,N,N',N'-tetramethyl-2-butene-1,4-diamine), Polyquaternium-2, (poly[bis(2-chloroethyl) ether-alt-1,3-bis[3-(dimethylamino)propyl]urea]), Polyquaternium-4, (hydroxyethyl cellulose dimethyl diallylammonium chloride copolymer; Diallyldimethylammonium chloride-hydroxyethyl cellulose copolymer), Polyquaternium-5 (copolymer of acrylamide and quaternized dimethylammoniumethyl methacrylate), polyquaternium-6 (poly(diallyldimethylammonium chloride)), Polyquaternium-7 (copolymer of acrylamide and diallyldimethylammonium chloride), Polyquaternium-8 (copolymer of methyl and stearyl dimethylaminoethyl ester of methacrylic acid, quaternized with dimethylsulphate), Polyquaternium-9 (homopolymer of N,N-(dimethylamino)ethyl ester of methacrylic acid, quaternized with bromomethane), Polyquaternium-10 (quaternized hydroxyethyl cellulose), polyquaternium-11 (copolymer of vinylpyrrolidone and quaternized dimethylaminoethyl methacrylate), Polyquaternium-12 (ethyl methacrylate/abietyl methacrylate/diethylaminoethyl methacrylate copolymer quaternized with dimethyl sulfate), Polyquaternium-13 (ethyl methacrylate/oleyl methacrylate/diethylaminoethyl methacrylate copolymer quaternized with dimethyl sulfate), Polyquaternium-14 (trimethylaminoethylmethacrylate homopolymer), Polyquaternium-15 (acrylamide-dimethylaminoethyl methacrylate methyl chloride copolymer), Polyquaternium-16 (copolymer of vinylpyrrolidone and quaternized vinylimidazole), Polyquaternium-17 (adipic acid, dimethylaminopropylamine and dichloroethylether copolymer), Polyquaternium-18 (azelanic acid, dimethylaminopropylamine and dichloroethylether copolymer), Polyquaternium-19 (copolymer of polyvinyl alcohol and 2,3-epoxypropylamine), Polyquaternium-20 (copolymer of polyvinyl octadecyl ether and 2,3-epoxypropylamine), Polyquaternium-22 (copolymer of acrylic acid and diallyldimethylammonium chloride), Polyquaternium-24 (quaternary ammonium salt of hydroxyethyl cellulose reacted with a lauryl dimethyl ammonium substituted epoxide), Polyquaternium-27 (block copolymer of Polyquaternium-2 and Polyquaternium-17), Polyquaternium-28 (copolymer of vinylpyrrolidone and methacrylamidopropyl trimethylammonium), Polyquaternium-29 (chitosan modified with propylene oxide and quaternized with epichlorhydrin), Polyquaternium-30 (ethanaminium, N-(carboxymethyl)-N,N-dimethyl-2-[(2-methyl-1-oxo-2-propen-1-yl)oxy]-, inner salt, polymer with methyl 2-methyl-2-propenoate), Polyquaternium-31 (N,N-dimethylaminopropyl-N-acrylamidine quatemized with diethylsulfate bound to a block of polyacrylonitrile), Polyquaternium-32 (poly(acrylamide 2-methacryloxyethyltrimethyl ammonium chloride)), Polyquaternium-33 (copolymer of trimethylaminoethylacrylate salt and acrylamide), Polyquaternium-34 (copolymer of 1,3-dibromopropane and N,N-diethyl-N',N'-dimethyl-1,3-propanediamine), Polyquaternium-35 (methosulphate of the copolymer of methacryloyloxyethyltrimethylammonium and of methacryloyloxyethyldimethylacetylammonium), Polyquaternium-36 (copolymer of N,N-dimethylaminoethylmethacrylate and buthylmethacrylate, quaternized with dimethylsulphate), Polyquaternium-37 (poly(2-methacryloxyethyltrimethylammonium chloride)), Polyquaternium-39 (terpolymer of acrylic acid, acrylamide and diallyldimethylammonium Chloride), Polyquaternium-42 (poly[oxyethylene(dimethylimino)ethylene (dimethylimino)ethylene dichloride]), Polyquaternium-43 (copolymer of acrylamide, acrylamidopropyltrimonium chloride, 2-amidopropylacrylamide sulfonate and dimethylaminopropylamine), Polyquaternium-44 (3-Methyl-1-vinylimidazolium methyl sulfate-N-vinylpyrrolidone copolymer), Polyquaternium-45 (copolymer of (N-methyl-N-ethoxyglycine)methacrylate and N,N-dimethylaminoethylmethacrylate, quaternized with dimethyl sulphate), Polyquaternium-46 (terpolymer of vinylcaprolactam, vinylpyrrolidone, and quaternized vinylimidazole), and Polyquaternium-47 (terpolymer of acrylic acid, methacrylamidopropyl trimethylammonium chloride, and methyl acrylate).

In some embodiments, the cleansing compositions of the instant disclosure include one or more cationic polymers selected from cationic cellulose derivatives, quaternized hydroxyethyl cellulose (e.g., polyquaternium-10), cationic starch derivatives, copolymers of acrylamide and dimethyldiallyammonium chloride (e.g., polyquaternium-7), and a combination thereof. In one particularly preferred embodiment, the cationic polymer(s) are selected from polyquaterniums, for example, polyquaterniums selected from polyquaternium-4, polyquaternium-5, polyquaternium-6, polyquaternium-7, polyquaternium-10, polyquaternium-22, polyquaternium-37, polyquaternium-39, polyquaternium-47, polyquaternium-53, and a combination thereof. In particular, polyquaternium-7 and/or polyquaternium-10 can be particularly useful.

Other cationic polymers that can be used include polysaccharide polymers, such as cationic cellulose derivatives and cationic starch derivatives. Cationic cellulose is available from Amerchol Corp. (Edison, N.J., USA) in its "Polymer JR" (trademark) and "Polymer LR" (trademark) series of polymers, as salts of hydroxyethyl cellulose reacted with trimethyl ammonium substituted epoxide (referred to as "Polyquaternium-10"). Another type of cationic cellulose includes the polymeric quaternary ammonium salts of hydroxyethyl cellulose reacted with lauryl dimethyl ammonium-substituted epoxide (referred to as "Polyquaternium-24"). These materials are available from Amerchol Corp. (Edison, N.J., USA) under the tradename "Polymer LM-200."

As emphasized throughout the disclosure, the one or more cationic polymers other than a cationic guar is preferably a cationic polysaccharide, more preferably a cationic cellulose. The cationic celluloses include cellulose ethers comprising quaternary ammonium groups, cationic cellulose copolymers, or celluloses grafted with a water-soluble quaternary ammonium monomer. Preferred cationic celluloses include polyquaternium-4, polyquaternium-10, polyquaternium-24, polyquaternium-67, and combinations thereof, more preferably polyquaternium-10 (quaternized hydroxyethyl cellulose).

The total amount of the one or more cationic polymers other than a cationic guar will vary but is typically in an amount from about 0.01 to about 10 wt. %, based on a total weight of the cleansing composition. In further embodiments, the total amount of the one or more cationic polymers other than a cationic guar is from about 0.01 to about 5 wt. %, about 0.01 to about 3 wt. %, about 0.01 to about 2 wt. %, about 0.01 to about 1 wt. %, about 0.05 to about 10 wt. %, about 0.05 to about 5 wt. %, about 0.05 to about 3 wt. %, about 0.05 to about 2 wt. %, about 0.05 to about 1 wt. %, about 0.1 to about 5 wt. %, or about 0.1 to about 3 wt. %, about 0.1 to about 2 wt. %, or about 0.1 to about 1 wt. %, based on the total weight of the cleansing composition. In a preferred embodiment, the cleansing composition includes about 0.01 to about 5 wt. %, preferably about 0.1 to about 4 wt. %, more preferably about 0.2 to about 3 wt. % of the one or more cationic polymers other than a cationic guar, based on the total weight of the cleansing composition.

(f) Water

The total amount of water in the cleansing compositions will vary but is typically from about 50 to about 85 wt. %, based on a total weight of the cleansing composition. In further embodiments, the cleansing composition includes about 50 to about 80 wt. %, about 50 to about 75 wt. %, about 55 to about 85 wt. %, about 55 to about 80 wt. %, about 55 to about 75 wt. %, about 60 to about 85 wt. %, about 60 to about 80 wt. %, about 60 to about 75 wt. %, about 65 to about 85 wt. %, about 65 to about 80 wt. %, or about 65 to about 75 wt. %, based on a total weight of the cleansing composition. In a preferred embodiment, the cleansing composition includes from about 50 to about 85 wt. %, preferably from about 60 to about 80 wt. %, and more preferably from about 65 to about 75 wt. % of water, based on the total weight of the cleansing composition.

(d) Fatty Compounds

The term "fatty compound" is interchangeable with the term "fatty substance," and means a compound that is insoluble in water at ordinary temperature (25° C.) and at atmospheric pressure (760 mmHg), i.e. which has a solubility of less than 5%, preferably less than 1% and even more preferentially less than 0.1%. They may have in their structure a hydrocarbon-based chain containing at least 6 carbon atoms. In various embodiments, the one or more fatty compounds other than the fatty alcohol of (a) may exclude silicones. Likewise, in preferred embodiments, the cleansing composition are free or essentially free from silicones. "Silicones" refers to a class of synthetic polymers that are based on a framework of alternating silicon and oxygen (siloxane) bonds with at least one organic group attached to the silicon atom via a direct carbon-silicon bond. Nonlimiting examples of fatty compounds include fatty esters, fatty ethers, propylene glycol fatty acid esters, fatty carbonate esters, oils, waxes, fatty alcohols, and fatty acids.

i. Fatty Esters

Non-limiting examples of fatty esters include fatty esters from a $C_6$-$C_{32}$ fatty acid and/or a $C_6$-$C_{32}$ fatty alcohol. These esters may be esters of saturated or unsaturated, linear or branched $C_1$-$C_{26}$ aliphatic mono or polyacids and of saturated or unsaturated, linear or branched $C_1$-$C_{26}$ aliphatic mono or polyalcohols, the total number of carbon atoms in the esters being greater than or equal to 10. In some cases, for the esters of monoalcohols, at least one of the alcohol or the acid from which the esters of the invention result is branched. Among the monoesters of monoacids and of monoalcohols, mention may be made of ethyl palmitate, isopropyl palmitate, alkyl myristates such as isopropyl myristate or ethyl myristate, isocetyl stearate, 2-ethylhexyl isononanoate, isononyl isononanoate, isodecyl neopentanoate, and isostearyl neopentanoate. Useful fatty esters include diesters of propylene glycol. Nonlimiting examples include propylene glycol dicaproate, propylene glycol dicaprylate, propylene glycol didecanoate, propylene glycol dilaurate, propylene glycol dimyristate, propylene glycol dipalmitate, propylene glycol distearate, propylene glycol dioleate, and propylene glycol dilinoleate. In various embodiments, the cleansing composition preferably includes at least one diesters of propylene glycol, preferably glycol distearate.

In various embodiments, the compositions of the instant disclosure may include cetyl esters. Cetyl esters are a mixture of the following esters of saturated fatty acids and fatty alcohols: cetyl palmitate, cetyl stearate, myristyl myristate, myristyl stearate, cetyl myristate, and stearyl stearate.

Mention is made of esters of $C_4$-$C_{22}$ dicarboxylic or tricarboxylic acids and of $C_1$-$C_{22}$ alcohols and esters of monocarboxylic, dicarboxylic or tricarboxylic acids and of $C_4$-$C_{26}$ dihydroxy, trihydroxy, tetrahydroxy or pentahydroxy non-sugar alcohols may also be used. Mention may be made in particular of diethyl sebacate, diisopropyl sebacate, diisopropyl adipate, di-n-propyl adipate, triisopropyl citrate, glyceryl trilactate, glyceryl trioctanoate, neopentyl glycol diheptanoate, and diethylene glycol diisononanoate.

Nonlimiting examples of liquid esters (ester oils) or liquid fatty esters that may be mentioned include, for example, sunflower oil, corn oil, soybean oil, marrow oil, grapeseed oil, sesame seed oil, hazelnut oil, apricot oil, macadamia oil, arara oil, castor oil, avocado oil, olive oil, rapeseed oil, coconut oil, wheatgerm oil, sweet almond oil, apricot oil, safflower oil, candlenut oil, coconut oil, camellina oil, tamanu oil, babassu oil and pracaxi oil, jojoba oil, and shea butter oil, and caprylic/capric triglyceride.

Nonlimiting examples of solid fatty esters include solid esters obtained from $C_9$-$C_{26}$ fatty acids and from $C_9$-$C_{26}$ fatty alcohols. Among these esters, mention may be made of octyldodecyl behenate, isocetyl behenate, cetyl lactate, stearyl octanoate, octyl octanoate, cetyl octanoate, decyl oleate, myristyl stearate, octyl palmitate, octyl pelargonate, octyl stearate, alkyl myristates such as cetyl myristate, myristyl myristate or stearyl myristate, and hexyl stearate.

In a preferred embodiment, at least one of the one or more emollients is selected from cetyl esters, purcellin oil (cetearyl octanoate), isopropyl myristate, isopropyl palmitate, C12-C15 alkyl benzoate, 2-ethylphenyl benzoate, isopropyl lanolate, hexyl laurate, diisopropyl adipate, isononyl isononanoate, oleyl erucate, 2-ethylhexyl palmitate, isostearyl isostearate, diisopropyl sebacate, octanoates, decanoates or ricinoleates of alcohols or polyalcohols, hydroxylated esters, pentaerythritol esters, diisostearyl malate, neopentyl glycol dioctanoate, dibutyl sebacate, di-C12-13 alkyl malate, dicetearyl dimer dilinoleate, dicetyl adipate, diisocetyl adipate, diisononyl adipate, diisostearyl dimer dilinoleate, diisostearyl fumarate, and a combination thereof.

The esters of fatty acids and/or of fatty alcohols, are esters of saturated or unsaturated, linear or branched C1-C26 aliphatic mono- or polyacids and of saturated or unsaturated, linear or branched C1-C26 aliphatic mono- or polyalcohols, the total carbon number of the esters more particularly being greater than or equal to 10. Among the monoesters, mention may be made of dihydroabietyl behenate; octyldodecyl behenate; isocetyl behenate; cetyl lactate; C12-C15 alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate. Still within the context of this variant, esters of C4-C22 dicarboxylic or tricarboxylic acids and of C1-C22 alcohols and esters of mono-, di- or tricarboxylic acids and of C2-C26 di-, tri-, tetra- or pentahydroxy alcohols may also be used.

ii. Fatty Ethers

Nonlimiting examples of fatty ethers include olyoxyethylene cetyl/stearyl ether, polyoxyethylene cholesterol ether, polyoxyethylene laurate or dilaurate, polyoxyethylene stearate or distearate, polyoxyethylene lauryl or stearyl ether, dicaprylyl ether, dicetyl ether distearyl ether, dodecyl ether, dilauryl ether, dimyristyl ether, diisononyl ether, or a combination thereof. Non-limiting examples of suitable polyoxyethylene fatty ethers include, but are not limited to, polyoxyethylene cetyl/stearyl ether, polyoxyethylene cholesterol ether, polyoxyethylene laurate or dilaurate, polyoxyethylene stearate or distearate, polyoxyethylene lauryl or stearyl ether, and combinations thereof, wherein the polyoxyethylene head group ranges from about 2 to about 100 groups. In certain embodiments, the polyoxyethylene fatty ethers include polyoxyethylene stearyl ether, polyoxyethylene myristyl ether, polyoxyethylene lauryl ether having from about 3 to about 10 oxyethylene units and combinations thereof. In yet another embodiment, at least one of the emollients is a fatty ether selected from stearyl ether, dicaprylyl ether, dicetyl ether, distearyl ether, dodecyl ether, dilauryl ether, dimyristyl ether, diisononyl ether, or a combination thereof.

iii. Propylene Glycol Fatty Acid Esters

Nonlimiting examples of propylene glycol fatty acid esters include propylene glycol esters of medium chain fatty acids (fatty acids having from 6 to 12 carbon atoms), such as propylene glycol dicaprylate/dicaprate, propylene glycol dipelargonate, and propylene glycol dilaurate. A preferred propylene glycol fatty acid ester is propylene glycol dicaprylate/dicaprate. The term "propylene glycol dicaprylate/dicaprate" is understood by those in the art to refer to a combination containing propylene glycol dicaprylate, propylene glycol dicaprylate-caprate, and propylene glycol dicaprate, which may vary in the ratio of these components. An example of a commercially available form of propylene glycol dicaprylate/dicaprate is "CAPTEX® 200," available from the Abitec Corp. (Columbus, OH, USA).

iv. Fatty Carbonate Esters

Nonlimiting examples of fatty carbonate esters include dialkyl carbonates of formula: $R_1O(C{=}O)R_2$, wherein $R_1$ and $R_2$ are independently linear or branched, saturated or unsaturated alkyl chains having 1 to 30 carbon atoms, or having 2 to 28 carbon atoms, or having 4 to 25 carbon atoms, or having 6 to 22 carbon atoms, preferably one or more fatty carbonates selected from C14-15 dialkyl carbonate, dicaprylyl carbonate, diethyl carbonate, dihexyl carbonate, diethylhexyl carbonate, dimethoxyphenyl phenyloxoethyl ethylcarbonate, dimethyl carbonate, dipropyl carbonate, dipropylheptyl carbonate, dioctyl carbonate, and a combination thereof.

iv. Oils

The term "oil" means any fatty substance that is in liquid form at room temperature (20-25° C.) and at atmospheric pressure. The one or more oils can be hydrocarbon-based oils, fluoro oils, non-fluoro oils, or combinations thereof. The term "hydrocarbon-based oil" is interchangeable with the term "hydrocarbon oil." The one or more oils can be "volatile oils" or "non-volatile oils." For the purposes of the instant disclosure, the term "volatile oil" means an oil (or non-aqueous medium) capable of evaporating on contact with the skin in less than one hour, at room temperature and at atmospheric pressure. The volatile oil is a volatile cosmetic oil, which is liquid at room temperature, especially having a non-zero vapour pressure, at room temperature and atmospheric pressure, in particular having a vapour pressure ranging from 0.13 Pa to 40 000 Pa (10-3 to 300 mmHg), preferably ranging from 1.3 Pa to 13 000 Pa (0.01 to 100 mmHg), and preferentially ranging from 1.3 Pa to 1300 Pa (0.01 to 10 mmHg).

Suitable oils include, but are not limited to, natural oils, such as coconut oil; hydrocarbons, such as mineral oil and hydrogenated polyisobutene; fatty alcohols, such as octyldodecanol; esters, such as $C_{12}$-$C_{15}$ alkyl benzoate; diesters, such as propylene dipelarganate; and triesters, such as glyceryl trioctanoate. Non-limiting examples of oils that may, optionally, be included in the hair treatment compositions include isotridecyl isononanoate, PEG-4 diheptanoate, isostearyl neopentanoate, tridecyl neopentanoate, cetyl octanoate, cetyl palmitate, cetyl ricinoleate, cetyl stearate, cetyl myristate, coco-caprylate/caprate, coco-dicaprylate/caprate, decyl isostearate, isodecyl oleate, isodecyl neopentanoate, isohexyl neopentanoate, octyl palmitate, dioctyl malate, tridecyl octanoate, myristyl myristate, octododecanol, or combinations of octyldodecanol, acetylated lanolin alcohol, cetyl acetate, isododecanol, polyglyceryl-3-diisostearate, castor oil, lanolin and lanolin derivatives, triisocetyl citrate, sorbitan sesquioleate, $C_{10}$-$C_{18}$ triglycerides, caprylic/capric/triglycerides, coconut oil, corn oil, cottonseed oil, glyceryl triacetyl hydroxystearate, glyceryl triacetyl ricinoleate, glyceryl trioctanoate, hydrogenated castor oil, linseed oil, mink oil, olive oil, palm oil, illipe butter, rapeseed oil, soybean oil, sunflower seed oil, tallow, tricaprin, trihydroxystearin, triisostearin, trilaurin, trilinolein, trimyristin, triolein, tripalmitin, tristearin, walnut oil, wheat germ oil, cholesterol, or combinations thereof.

The triglyceride oils of plant or synthetic origin are preferably chosen from liquid fatty acid triglycerides comprising from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names "Miglyol® 810," "Miglyol® 812," and "Miglyol® 818" by the company Dynamit Nobel, jojoba oil and shea butter oil. In a preferred embodiment, the cleansing composition includes one or more oils, preferably one or more natural oils, more preferably one or more plant (vegetable or vegetal) oils, for example, sunflower oil, corn oil, soybean oil, marrow oil, grapeseed oil, shea butter, coco-caprylate/caprate, or combinations thereof.

The fluoro oils may be chosen from perfluoromethylcyclopentane and perfluoro-1,3-dimethylcyclohexane, sold under the names "Flutec® PC1" and "Flutec® PC3" by the company, BNFL Fluorochemicals; perfluoro-1,2-dimethylcyclobutane; perfluoroalkanes such as dodecafluoropentane and tetradecafluorohexane, sold under the names "PF 5050@" and "PF 5060@" by the company, 3M, or bromoperfluorooctyl sold under the name "Foralkyl®" by the company, Atochem; nonafluoromethoxybutane and nonafluoroethoxyisobutane; perfluoromorpholine derivatives such as 4-trifluoromethyl perfluoromorpholine sold under the name "PF 5052@" by the company, 3M.

v. Waxes

Waxes are solids at room temperature and typically have a melting point greater than 30° C. or greater than 30° C. to about 100° C. Natural waxes include animal, vegetable/plant, mineral, or petroleum derived waxes. They are typically esters of fatty acids and long chain alcohols. Wax esters are derived from a variety of carboxylic acids and a variety of fatty alcohols.

Non-limiting examples of waxes include aliphatic esters, such as cetyl esters, stearyl esters, acacia, beeswax, ceresin, flower wax, citrus wax, carnauba wax, jojoba wax, Japanese wax, polyethylene, microcrystalline, rice bran, lanolin wax, mink, montan, bayberry, ouricury, ozokerite, palm kernel wax, paraffin, avocado wax, apple wax, shellac wax, salvia wax, candelilla wax, their polyalkylene glycol derivatives (e.g., PEG 6-20 beeswax or PEG-12 carnauba wax), and mixtures of any of the aforementioned waxes.

Additional nonlimiting examples of waxes include beeswax, hydrogenated alkyl olive esters (commercially available under the tradename "Phytowax® Olive"), carnauba wax, candelilla wax, ouricury wax, Japan wax, cork fibre wax or sugar cane wax, rice wax, montan wax, paraffin wax, lignite wax or microcrystalline wax, ceresin or ozokerite, palm kernel glycerides/hydrogenated palm glycerides and hydrogenated oils such as hydrogenated castor oil or jojoba oil, sugarcane, retamo, bayberry, rice bran, soy, castor, esparto, hydroxyoctacosanyl hydroxystearate, Chinese wax, cetyl palmitate, lanolin, shellac, and spermaceti; synthetic waxes such as those of the hydrocarbon type and polyethylene waxes obtained from the polymerization or copolymerization of ethylene, and Fischer-Tropsch® waxes, or else esters of fatty acids, such as octacosanyl stearate, glycerides which are solid at temperatures of above 30° C.

v. Fatty Alcohols

The term "fatty alcohol" means an alcohol comprising at least one hydroxyl group (OH), and comprising at least 8 carbon atoms, and which is neither oxyalkylenated (in particular neither oxyethylenated nor oxypropylenated) nor glycerolated. The fatty alcohols can be represented by: R—OH, wherein R denotes a saturated (alkyl) or unsaturated (alkenyl) group, linear or branched, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms.

In various embodiments, the compositions include at least one solid fatty alcohol. Solid fatty alcohols are fatty alcohols that are solid at ambient temperature and at atmospheric pressure (25° C., 780 mmHg), and are insoluble in water, i.e., they have a water solubility of less than 1% by weight, preferably less than 0.5% by weight, at 25° C., 1 atm. The solid fatty alcohols may be represented by: R—OH, wherein R denotes a linear alkyl group, optionally substituted with one or more hydroxyl groups, comprising from 8 to 40 carbon atoms, preferably 10 to 30 carbon atoms, more preferably 12 to 24 carbon atoms, and even more preferably 14 to 22 carbon atoms. Nonlimiting examples include lauryl alcohol (1-dodecanol); myristyl alcohol (1-tetradecanol), cetyl alcohol (1-hexadecanol), stearyl alcohol (1-octadecanol), arachidyl alcohol (1-eicosanol), behenyl alcohol (1-docosanol), lignoceryl alcohol (1-tetracosanol), ceryl alcohol (1-hexacosanol), montanyl alcohol (1-octacosanol), myricylic alcohol (1-triacontanol), and combinations thereof. In a preferred embodiment, the compositions include at least one solid fatty alcohol selected from myristyl alcohol, cetyl alcohol, stearyl alcohol, behenyl alcohol and combinations thereof such as cetylstearyl or cetearyl alcohol.

In various embodiments, the compositions include at least one liquid fatty alcohol, in particular containing C10-C34 and preferably have branched carbon chains and/or have one or more, preferably 1 to 3 double bonds. They are preferably branched and/or unsaturated (C═C double bond) and contain from 12 to 40 carbon atoms. The liquid fatty alcohols may be represented by: R—OH, wherein R denotes a C12-C24 branched or straight alkyl group or an alkenyl group, R being optionally substituted by one or more hydroxy groups. In certain embodiments, the liquid fatty alcohols are selected from branched saturated alcohols. Preferably, R does not contain a hydroxyl group. Nonlimiting examples include oleyl alcohol, linoleyl alcohol, linolenyl alcohol, isocetyl alcohol, isostearyl alcohol, 2-octyl-1-dodecanol, 2-butyloctanol, 2-hexyl-1-decanol, 2-decyl-1-tetradecanol, 2-tetradecyl-1-cetanol and combinations thereof. In other embodiments, the compositions are free or essentially free from liquid fatty alcohols, including the liquid fatty alcohols referenced above.

In a preferred embodiment, the one or more fatty alcohols are linear (straight chain) saturated fatty alcohols having from 10 to 30 carbon atoms, preferably from 12 to 28 carbon atoms, more preferably from 14 to 24 carbon atoms. Nonlimiting examples include decyl alcohol, undecyl alcohol, dodecyl alcohol, myristyl alcohol, cetyl alcohol, stearyl alcohol, cetearyl alcohol, behenyl alcohol, myricyl alcohol and a combination thereof.

(vi) Fatty Acids

A fatty acid is a carboxylic acid with an aliphatic chain, for example, of 8 to 30 carbon atoms, preferably 8 to 28 carbon atoms, more preferably from 12 to 26 carbon atoms, which is either saturated or unsaturated, and branched or unbranched. Most naturally occurring fatty acids have an unbranched chain of an even number of carbon atoms, from 6 to 28. In some embodiments, naturally occurring fatty acids are preferred.

Nonlimiting examples of fatty acids include caprylic acid, capric acid, lauric acid, myristic acid, palmitic acid, stearic acid, arachidic acid, behenic acid, lignoceric acid, cerotic acid, myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, isostearic acid, and a combination thereof.

In a preferred embodiment, the one or more fatty acids are selected from unsaturated fatty acids, preferably monounsaturated fatty acids. Unsaturated fatty acid carbon chains contain one or more double bonds with a terminal carboxylic group (—COOH). A fatty acid with a single double bond is termed "monounsaturated fatty acid," and fatty acids with more than one double bond are termed "polyunsaturated fatty acids." Nonlimiting examples of unsaturated fatty acids include myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, and a combination thereof. In a preferred embodiment, the one or more fatty acids includes oleic acid, and optionally one or more additional fatty acids.

In a preferred embodiment, the one or more fatty acids are selected from non-linear fatty acids. The term "non-linear fatty acids" as used in the instant disclosure refers to unsaturated fatty acid and/or branched fatty acids. Unsaturated fatty acid carbon chains contain one or more double bonds with a terminal carboxylic group (—COOH). A fatty acid with a single double bond is termed "monounsaturated fatty acid," and fatty acids with more than one double bond are termed "polyunsaturated fatty acids." Nonlimiting examples of unsaturated fatty acids include myristoleic acid, palmitoleic acid, sapienic acid, oleic acid, elaidic acid, vaccenic acid, linoleic acid, linoelaidic acid, α-linolenic acid, arachidonic acid, eicosapentaenoic acid, erucic acid, docosahexaenoic acid, and a combination thereof. In a preferred embodiment, the one or more fatty acids includes oleic acid, and optionally one or more additional fatty acids.

Nonlimiting examples of branched fatty acids include isostearic acid, isolauric acid, isomyristic acid, isopalmitic acid, and a combination there.

The total amount of the one or more fatty compounds in the cleansing composition will vary but is typically in an amount from about 0.01 to about 8 wt. %, based on the total weight of the cleansing composition. In further embodiments, the cleansing composition includes about 0.01 to about 6 wt. %, about 0.1 to about 5 wt. %, about 0.2 to about 3 wt. %, or about 0.5 to about 2 wt. % of the one or more fatty compounds. In a preferred embodiment, the cleansing composition includes about 0.1 to about 5 wt. %, preferably about 0.2 to about 4 wt. %, and more preferably about 0.5 to about 2 wt. % of the one or more fatty compounds, based on the total weight of the cleansing composition.

(h) Water-Soluble Solvents

The term "water soluble solvent" is interchangeable with the terms "water soluble organic solvent" and "water-miscible solvent" and means a compound that is liquid at 25° C. and at atmospheric pressure (760 mmHg) and has a solubility of at least 50% in water under these conditions. In some cases, the water-soluble solvent has a solubility of at least 60%, 70%, 80%, or 90%. Non-limiting examples of water-soluble solvents include, for example, organic solvents selected from glycerin, alcohols (for example $C_{2-8}$, monoalcohols), polyols (polyhydric alcohols), glycols, and a combination thereof.

Non-limiting examples of water-soluble organic solvents include, for example, organic solvents selected from glycerin, alcohols (for example, $C_{1-10}$, $C_{1-8}$, or $C_{1-4}$ alcohols), polyols (polyhydric alcohols), glycols, and a combination thereof. Nonlimiting examples of monoalcohols and polyols include ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin.

Further non-limiting examples of water soluble organic solvents include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a combination thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a combination thereof. Polyol compounds may also be used. Non-limiting examples include the aliphatic diols, such as 2-ethyl-2-methyl-1,3-propanediol, 3,3-dimethyl-1, 2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a combination thereof.

In a preferred embodiment, the hair treatment composition includes one or more glycols selected from glycerin, propylene glycol, butylene glycol, pentylene glycol, hexylene glycol, caprylyl glycol, dipropylene glycol, a $C_2$-$C_6$ monoalcohol (such as ethanol or isopropanol), and combinations thereof.

The total amount of the one or more water-soluble solvents in the hair treatment composition will vary. Nonetheless, in various embodiments, the hair treatment composition includes about 0.1 to about 15 wt. % of the one or more water soluble solvents, based on the total weight of the hair treatment compositions. In further embodiments, the hair treatment composition includes about 0.1 to about 10 wt. %, about 0.1 to about 8 wt. %, about 0.1 to about 5 wt. %, about 0.1 to about 3 wt. %, about 0.5 to about 10 wt. %, about 0.5 to about 8 wt. %, about 0.5 to about 5 wt. %, or about 0.5 to about 3 wt. % of the one or more water soluble solvents, based on the total weight of the cleansing composition.

(i) Non-Cationic Thickening Polymers

The cleansing compositions may optionally include or exclude one or more non-cationic thickening polymers (also referred to as thickeners or viscosity modifying agents). Many non-cationic thickening polymers are water-soluble and increase the viscosity of water or form an aqueous gel when dispersed/dissolved in water. The aqueous solution may be heated and cooled, or neutralized, for forming a gel, if necessary. The non-cationic thickening polymers may be dispersed/dissolved in an aqueous solvent that is soluble in water, e.g., ethyl alcohol when it is dispersed/dissolved in water.

Carboxylic Acid Polymers

These polymers are crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol.

Nonlimiting of commercially available carboxylic acid polymers useful herein include the carbomers, which are homopolymers of acrylic acid crosslinked with allyl ethers of sucrose or pentaerytritol. The carbomers are available as the "Carbopol™ 900" series from B.F. Goodrich (e.g., "Carbopol® 954"). In addition, other suitable carboxylic acid polymeric agents include "Ultrez® 10" (B.F. Goodrich) and copolymers of C10-30 alkyl acrylates with one or more monomers of acrylic acid, methacrylic acid, or one of their short chain (i.e., C1-4 alcohol) esters, wherein the crosslinking agent is an allyl ether of sucrose or pentaerytritol. These copolymers are known as acrylates/C10-C30 alkyl acrylate crosspolymers and are commercially available as "Carbopol® 1342," "Carbopol® 1382," "Pemulen TR-1", and "Pemulen TR-2" from B.F. Goodrich. In other words, examples of carboxylic acid polymer thickeners useful herein are those selected from carbomers, acrylates/C10-C30 alkyl acrylate crosspolymers, and combinations thereof.

In a preferred embodiment, the cleansing compositions include one or more carboxylic acid polymers, preferably wherein the carboxylic acid polymers are selected from crosslinked compounds containing one or more monomers derived from acrylic acid, substituted acrylic acids, or salts and esters of these acrylic acids and the substituted acrylic acids, wherein the crosslinking agent contains two or more carbon-carbon double bonds and is derived from a polyhydric alcohol. Even more preferably, the cleansing composition includes acrylates/C10-C30 alkyl acrylate crosspolymer.

Further nonlimiting examples of thickening agents include crosslinked polyacrylate polymers, polyacrylamide polymers, polysaccharides, and gums, as set forth below.

Crosslinked Polyacrylate Polymers

The cleansing compositions of the present disclosure may optionally contain crosslinked polyacrylate polymers useful as thickeners or gelling agents provided they are nonionic polymers.

Polyacrylamide Polymers

The cleansing compositions of the present disclosure may optionally contain polyacrylamide polymers, especially polyacrylamide polymers including substituted branched or unbranched polymers. Among these polyacrylamide polymers is the polymer given the CTFA designation polyacrylamide and isoparaffin and laureth-7, available under the tradename "Sepigel 305" from Seppic Corporation.

Other polyacrylamide polymers useful herein include multi-block copolymers of acrylamides and substituted acrylamides with acrylic acids and substituted acrylic acids. Commercially available examples of these multi-block copolymers include "Hypan SR150H," "Hypan SS500V," Hypan SS500W," and "Hypan SSSA100H" from Lipo Chemicals, Inc.

The compositions may also contain thickening and texturizing gels of the type as exemplified by the product range called "Lubrajel®" from United Guardian. These gels have moisturizing, thickening, and stabilizing properties.

Polysaccharides

A wide variety of polysaccharides can be useful. "Polysaccharides" refer to gelling agents that contain a backbone of repeating sugar (i.e., carbohydrate) units. Nonlimiting examples of polysaccharide gelling agents include those selected from the group cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and combinations thereof. Also useful herein are the alkyl-substituted celluloses. Preferred among the alkyl hydroxyalkyl cellulose ethers is the material given the CTFA designation cetyl hydroxyethylcellulose, which is the ether of cetyl alcohol and hydroxyethylcellulose. This material is sold under the tradename "Natrosol® CS Plus" from Aqualon Corporation.

Other useful polysaccharides include scleroglucans comprising a linear chain of (1-3) linked glucose units with a (1-6) linked glucose every three units, a commercially available example of which is "Clearogel™ CS11" from Michel Mercier Products Inc.

Gums

Other thickening and gelling agents useful herein include materials which are primarily derived from natural sources. Non-limiting examples of these gelling agent gums include acacia, agar, algin, alginic acid, ammonium alginate, amylopectin, calcium alginate, calcium carrageenan, carnitine, carrageenan, dextrin, gelatin, gellan gum, guar gum, hectorite, hyaluronic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboxymethyl dextran, sodium carrageenan, tragacanth gum, xanthan gum, biosaccharide gum, and combinations thereof.

Additional examples of water-soluble thickeners include water-soluble natural polymers, water-soluble synthetic polymers, clay minerals, and silicic anhydride. Non-limiting examples of water-soluble natural polymers include gum arabic, tragacanth gum, karaya gum, guar gum, gellan gum, tara gum, locust bean gum, tamarind gum, sodium alginate, alginic acid propyleneglycol ester, carrageenan, furcellaran, agar, high-methoxy pectin, low-methoxy pectin, xanthine, chitosan, starch (for example starch derived from corn, potato, wheat, rice, sweet potato and tapioca, a-starch, soluble starch), fermentation polysaccharide (for example, xanthan gum, pullulan, carciran, dextran), acidic heteropolysaccharide derived from callus of plants belonging to Polyantes sp. (for example, tuberous polysaccharide), proteins (for example, sodium casein, gelatin, albumin), chondroitin sulfate, and hyaluronic acid.

Non-limiting examples of water-soluble synthetic polymers include polyvinyl alcohol, sodium polyacrylate, sodium polymethacrylate, polyacrylic acid glycerin ester, carboxyvinyl polymer, polyacrylamide, polyvinyl pyrrolidone, polyvinyl methylether, polyvinyl sulfone, maleic acid copolymer, polyethylene oxide, polydiallyl amine, polyethylene imine, water soluble cellulose derivatives (for example, carboxymethyl cellulose, methyl cellulose, methylhydroxypropyl cellulose, hydroxyethyl cellulose, hydroxypropyl cellulose, cellulose sulfate sodium salt), and starch derivatives (for example, starch oxide, dialdehyde starch, dextrin, British gum, acetyl starch, starch phosphate, carboxymethyl starch, hydroxyethyl starch, and hydroxypropyl starch).

Preferably, the cleansing composition includes acrylates/C10-C30 alkyl acrylate crosspolymer.

The total amount of the one or more non-cationic thickening polymers in the cleansing compositions, if present, may vary but is typically in an amount of from about 0.01 to about 10 wt. %, from based on the total weight of the cleansing composition. In some embodiments, the total amount of non-cationic thickening polymers in the cleansing composition is from about 0.01 to about 5 wt. %, from about 0.01 to about 3 wt. %, from about 0.05 to about 10 wt. %, from about 0.05 to about 5 wt. %, from about 0.05 to about 3 wt. %, about 0.05 to about 2 wt. %, about 0.05 to about 1 wt. %, from about 0.1 to about 10 wt. %, from about 0.1 to about 5 wt. %, or from about 0.1 to about 3 wt. %, about 0.1 to about 2 wt. %, or about 0.1 to about 1 wt. % of the one or more thickening agents, based on the total weight of the cleansing composition.

(j) Miscellaneous Ingredients

The cleansing compositions may optionally include (or optionally exclude) one or more miscellaneous ingredients. Miscellaneous ingredients are ingredients that are compatible with the hair treatment compositions and do not disrupt or materially affect the basic and novel properties of the compositions. Nonlimiting examples of miscellaneous ingredients include preservatives, fragrances, pH adjusters, salts, chelating agents, buffers, antioxidants, flavonoids, vitamins, botanical extracts, UV filtering agents, proteins, protein hydrolysates and/or isolates, fillers (e.g., organic and/or inorganic fillers such as talc, calcium carbonate, silica, etc.) composition colorants, etc.

In various embodiments, the cleansing compositions of the instant disclosure include one or more miscellaneous ingredients selected from preservatives, fragrances, pH adjusters, salts, chelating agents, buffers, amino acids, composition colorants, fillers (such as talc, calcium carbonate, silica, including hydrated silica), vitamins, botanical extracts, and a combination thereof. For example, the cleansing compositions may include silica (or hydrated silica), tocopherol, fragrances, or a combination thereof.

In the context of the instant disclosure, a "composition colorant" is a compound that colors the composition but does not have an appreciable coloring effect on hair. In other words, the composition colorant is included to provide a color to the composition for aesthetic appeal but is not intended to impart coloring properties to hair. As an example, hair styling gels, can be found in a variety of different colors (e.g., light blue, light pink, etc.) yet application of the styling gel to hair does not visibly change the color of the hair.

In various embodiments, at least one of the one or more miscellaneous ingredients is a sugar alcohol and/or a mono or di-saccharide. Nonlimiting examples of sugar alcohols include sorbitol, mannitol, erythritol, and xylitol. Nonlimiting examples of mono and di-saccharides include glucose, fructose, galactose, and sucrose. The one or more sugar alcohol and/or mono/di saccharide may be in an amount of about 0.1 to about 5 wt. %, preferably about 0.5 to about 4 wt. %, and more preferably about 1 to about 3 wt. %, based on the total weight of the cleansing composition. In a preferred embodiment, the cleansing composition includes sorbitol.

In various embodiments, at least one of the one or more miscellaneous ingredients is urea or a urea compound, for example, an alkyl substituted urea, more particularly mono-substituted or di-substituted alkyl urea (e.g., hydroxyalkyl urea). The urea compound is preferably a hydroxyalkyl urea, such as hydroxyethyl urea. Preferably, the cleansing composition includes about 0.01 to 5 wt. %, preferably about 0.05 to about 3 wt. %, and more preferably about 0.1 to about 2 wt. % of a hydroxyalkyl urea, preferably hydroxyethyl urea.

The total amount of the one or more miscellaneous ingredients, if present, will vary. Nonetheless, in various embodiments, the cleansing compositions of the instant disclosure include from about 0.001 to about 10 wt. % of one or more miscellaneous ingredients, based on the total weight of the cleansing composition. In further embodiments, the cleansing compositions include from about 0.001 to about 5 wt. %, about 0.001 to about 3 wt. %, about 0.01 to about 10 wt. %, about 0.01 to about 5 wt. %, about 0.01 to about 3 wt. %, about 0.1 to about 10 wt. %, about 0.1 to about 5 wt. %, or about 0.1 to about 3 wt. % of one or more miscellaneous ingredients, including ranges and sub-ranges therebetween, based on the total weight of the cleansing composition.

Properties/Attributes

Unexpectedly, hair cleansed with the cleansing compositions of the instant disclosure requires less combing force to detangle than hair cleansed with typical cleansing compositions, especially when the hair is wet, immediately after rinsing the cleansing composition from the hair. Furthermore, hair cleansed with the cleansing composition of the instant disclosure exhibits improved frizz control, long-lasting curl definition, and a pleasant smoothness.

In a preferred embodiment, wet or damp hair cleansed with the cleansing composition of the instant disclosure requires less combing force to detangle (to comb through) than hair cleansed with a comparative cleansing composition without the hydroxypropyl guar hydroxypropyltrimonium chloride but otherwise identical to the cleansing composition.

In another embodiment, wet or damp hair cleansed with the cleansing composition of the instant disclosure requires less combing force to detangle (to comb through) than hair cleansed with a comparative cleansing composition without the one or more cationic polymers other than a cationic guar but otherwise identical to the cleansing composition.

In yet another embodiment, the one or more cationic polymers other than a cationic guar is a cationic cellulose, preferably a cationic cellulose selected from polyquaternium-4, polyquaternium-10, polyquaternium-24, polyquaternium-67, or a combination thereof (most preferably, polyquaternium-10), and wet or damp hair cleansed with the inventive cleansing composition requires less combing force to detangle (to comb through) than hair cleansed with a comparative cleansing composition without the one or more cationic celluloses but otherwise identical to the inventive cleansing composition.

Treatment with the cleansing compositions of the instant disclosure can provide at least a 10% reduction in combing force compared to the comparative compositions set forth in the embodiments above. Similarly, treatment with the cleansing compositions of the instant disclosure can provide at least a 15%, 20%, or 25%, or 30% reduction in combining force compared to the comparative compositions set forth in the embodiments above. Preferably, treatment with the cleansing compositions of the instant disclosure provides at least a 20%, more preferably at least a 25%, and even more preferably a 30% reduction in combining force compared to the comparative compositions set forth in the embodiments above.

Methods

The cleansing compositions of the instant disclosure are particularly useful for cleansing and conditioning hair or skin. Additionally, the cleansing compositions are useful for preserving color in artificially colored hair. The cleansing compositions provide a variety of desirable cosmetic and styling benefits to the hair, for example, smoothness, detangling, and shine. Accordingly, the cleansing compositions are useful in methods for cleansing hair and skin, methods of conditioning hair and skin, and methods for imparting smoothness, detangling, and/or shine to hair. In addition, the cleansing compositions are useful in methods of preserving color of artificially colored hair. The methods typically comprise application of the cleansing composition to the hair (or skin). The cleansing compositions can be massed or spread throughout the hair (or skin) and subsequently rinsed from the hair (or skin).

In some cases, the methods include shampooing and/or conditioning the hair with a cleansing composition of the instant disclosure. Such methods typically include applying an effective amount of a cleansing composition to the hair, massaging or spreading the composition throughout the hair, and subsequently rinsing the cleansing composition from the hair. Usually, the cleansing composition is merely allowed to remain on the hair for a period sufficient to incorporate the cleansing composition throughout the hair, for example, by lathering the composition throughout the hair using one's hands. As is common when using shampoo and/or conditioning compositions, the hair may be wetted or rinsed with water prior to application of a cleansing composition. Having water already in the hair can be helpful for creating lather when applying the cleansing compositions because the water interacts with the surfactants of the surfactant system.

Preferred Embodiments

In a preferred embodiment, the cleansing composition comprises, consists essentially of, or consists of:

(a) about 5 to about 20 wt. %, preferably about 5 to about 15, and more preferably about 8 to about 12 wt. % of a plurality of anionic surfactants comprising:
  (a)(i) about 5 to about 20 wt. %, preferably about 5 to about 15 wt. %, and more preferably about 8 to about 12 wt. % of one or more acyl isethionates, salts thereof, or combination thereof; and
  (a)(ii) about 0.1 to about 8 wt. %, preferably about 0.2 to about 5 wt. %, and more preferably about 0.5 to about 3 wt. % of one or more acyl amino acids, salts thereof, or combination thereof;
  (a)(iii) optionally, about 0.01 to about 8 wt. %, preferably about 0.0.05 to about 5 wt. %, and more preferably about 0.1 to about 4 wt. % of one or more additional anionic surfactants;

(b) about 1 to about 10 wt. %, preferably about 1 to about 8 wt. %, and more preferably about 2 to about 5 wt. % of one or more amphoteric surfactants;

(c) about 1 to about 15 wt. %, preferably about 3 to about 12 wt. %, and more preferably about 6 to about 12 wt. % of one or more nonionic surfactants, wherein at least one of the one or more nonionic surfactants is a polyglucoside, preferably in an amount of at least 5 wt. %, more preferably in an amount of at least 5 wt. % up to about 15 wt. %, and even more preferably in an amount of at least 8 wt. % up to about 12 wt. %;

wherein a total amount of (a), (b), and (c) is about 15 to about 40 wt. %, preferably an amount of about 15 to about 30 wt. %, and more preferably an amount of about 18 to about 28 wt. %;

(d) about 0.1 to about 5 wt. %, preferably about 0.2 to about 4 wt. %, and more preferably about 0.3 to about 2 wt. % of hydroxypropyl guar hydroxypropyltrimonium chloride;

(e) about 0.1 to about 5 wt. %, preferably about 0.1 to about 3 wt. %, and more preferably about 0.2 to about 2 wt. % of one or more cationic polymers other than a cationic guar;

(f) about 60 to about 85 wt. %, preferably about 65 to about 80 wt. %, and more preferably about 65 to about 75 wt. % of water;

(g) optionally, about 0.01 to about 8 wt. %, preferably about 0.1 to about 6 wt. %, and more preferably about 0.5 to about 5 wt. %, even more preferably about 0.5 to about 3 wt. % of one or fatty compounds;

(h) optionally, about 0.1 to about 15 wt. %, preferably about 0.1 to about 8 wt. %, and more preferably about 0.5 to about 5 wt. % of one or more water-soluble solvents;

(i) optionally, about 0.01 to about 5 wt. %, preferably about 0.05 to about 3 wt. %, and more preferably about 0.05 to about 1 wt. % of one or more non-cationic thickening polymers; and (j) optionally, about 0.1 to about 10 wt. %, preferably about 0.1 to about 8 wt. %, and more preferably about 1 to about 8 wt. % of one or more miscellaneous ingredients;

wherein all percentages by weight are based on a total weight of the cleansing composition;

and preferably, the cleansing composition is free or essentially free from sulfate-based anionic surfactants.

In a preferred embodiment, the cleansing composition comprises, consists essentially of, or consists of:

(a) about 5 to about 20 wt. %, preferably about 5 to about 15, and more preferably about 8 to about 12 wt. % of a plurality of anionic surfactants comprising:

(a)(i) about 5 to about 20 wt. %, preferably about 5 to about 15 wt. %, and more preferably about 8 to about 12 wt. % of one or more acyl isethionates selected from sodium isethionate, sodium cocoyl isethionate, sodium lauroyl methyl isethionate, sodium cocoyl methyl isethionate, or a combination thereof, more preferably wherein acyl isethionate is sodium or potassium cocoyl isethionate; and (a)(ii) about 0.1 to about 8 wt. %, preferably about 0.2 to about 5 wt. %, and more preferably about 0.5 to about 3 wt. % of one or more acyl amino acids, salts thereof, or combination thereof selected from acyl taurates, acyl glycinates, acyl glutamates, and acyl sarcosinates, salts thereof, or a combination thereof, preferably wherein at least one of the one or more acyl amino acids is an acyl glycinate, salt thereof, or combination thereof, more preferably wherein the acyl glycinate is selected from sodium cocoyl glycinate, sodium lauroyl glycinate, sodium myristoyl glycinate, potassium lauroyl glycinate, potassium cocoyl glycinate, or a combination thereof;

(a)(iii) optionally, about 0.01 to about 8 wt. %, preferably about 0.0.05 to about 5 wt. %, and more preferably about 0.1 to about 4 wt. % of one or more additional anionic surfactants, wherein the one or more additional anionic surfactants preferably include at least one non-sulfate-based anionic surfactant selected from salts of $C_8$-$C_{22}$ saturated or unsaturated fatty acids, and more preferably a cocoate selected from sodium cocoate, potassium cocoate, mono-, di- or tri-ethanolamine cocoate, or a combination thereof;

(b) about 1 to about 10 wt. %, preferably about 1 to about 8 wt. %, and more preferably about 2 to about 5 wt. % of one or more amphoteric surfactants selected from alkyl amphoproprionates, betaines, alkyl sultaines, alkyl amphoacetates, or a combination thereof, preferably wherein the one or more amphoteric surfactants include one or more betaines selected from coco betaine, cocamidopropyl betaine, lauryl betaine, laurylhydroxy sulfobetaine, lauryldimethyl betaine, cocamidopropyl hydroxysultaine, behenyl betaine, capryl/capramidopropyl betaine, lauryl hydroxysultaine, stearyl betaine, or a combination thereof;

(c) about 1 to about 15 wt. %, preferably about 3 to about 12 wt. %, and more preferably about 6 to about 12 wt. % of one or more nonionic surfactants, wherein at least one of the one or more nonionic surfactants is an alkyl polyglucoside, preferably in an amount of at least 5 wt. %, more preferably in an amount of at least 5 wt. % up to about 15 wt. %, and even more preferably in an amount of at least 8 wt. % up to about 12 wt. %, wherein the one or more alkyl polyglucosides are preferably selected from lauryl glucoside, octyl glucoside, decyl glucoside, coco glucoside, caprylyl/capryl glucoside, or a combination thereof;

wherein a total amount of (a), (b), and (c) is about 15 to about 40 wt. %, preferably an amount of about 15 to about 30 wt. %, and more preferably an amount of about 18 to about 28 wt. %;

(d) about 0.1 to about 5 wt. %, preferably about 0.2 to about 4 wt. %, and more preferably about 0.3 to about 2 wt. % of hydroxypropyl guar hydroxypropyltrimonium chloride;

(e) about 0.1 to about 5 wt. %, preferably about 0.1 to about 3 wt. %, and more preferably about 0.2 to about 2 wt. % of one or more cationic polymers other than a cationic guar, wherein at least one (or all) of the one or more cationic polymers other than a cationic guar are selected from cationic celluloses, preferably cationic celluloses selected from polyquaternium-4, polyquaternium-10, polyquaternium-24, polyquaternium-67, or a combination thereof, most preferably, polyquaternium-10;

(f) about 60 to about 85 wt. %, preferably about 65 to about 80 wt. %, and more preferably about 65 to about 75 wt. % of water;

(g) optionally, about 0.01 to about 8 wt. %, preferably about 0.1 to about 6 wt. %, more preferably about 0.5 to about 5 wt. %, and even more preferably about 0.5 to about 3 wt. % of one or fatty compounds selected from fatty esters, fatty ethers, propylene glycol fatty acid esters, fatty carbonate esters, oils, waxes, fatty alcohols, and fatty acids;

(h) optionally, about 0.1 to about 15 wt. %, preferably about 0.1 to about 8 wt. %, and more preferably about 0.5 to about 5 wt. % of one or more water-soluble solvents selected from glycerin, propylene glycol, butylene glycol, pentylene glycol, hexylene glycol, caprylyl glycol, dipropylene glycol, a $C_2$-$C_6$ monoalcohol (such as ethanol or isopropanol), and combinations thereof;

(i) optionally, about 0.01 to about 5 wt. %, preferably about 0.05 to about 3 wt. %, and more preferably about 0.05 to about 1 wt. % of one or more non-cationic thickening polymers, preferably wherein at least one of the one or more non-cationic thickening polymers is a carboxylic acid polymer, preferably wherein the carboxylic acid polymer is selected from crosslinked compounds containing one or more monomers derived from acrylic acid, substituted acrylic acids, or salts and esters of these acrylic acids and the substituted acrylic acids, wherein the crosslinking agent contains two or more carbon-carbon double bonds and is derived from a polyhydric alcohol, even more preferably wherein the non-cationic thickening polymers is acrylates/C10-C30 alkyl acrylate crosspolymer; and (j) optionally, about 0.1 to about 10 wt. %, preferably about 0.1 to about 8 wt. %, and more preferably about 1 to about 8 wt. % of one or more miscellaneous ingredients;

wherein all percentages by weight are based on a total weight of the cleansing composition, and preferably, the cleansing composition is free or essentially free from sulfate-based anionic surfactants.

EXAMPLES

Various changes can be made in the above-described compositions and methods without departing from the scope of the invention. Accordingly, it is intended that all disclosure contained in the above description and in the examples given below, shall be interpreted as illustrative and not in a limiting sense.

Example 1

Cleansing compositions of the present disclosure (A and B) and comparative composition (C-1 through C-6) were prepared according to the formulations described in Table I, below.

TABLE I

| | | | Cleansing Composition | | | | | | | |
|---|---|---|---|---|---|---|---|---|---|---|
| | | | Inventive | | Comparative | | | | | |
| | | | A | B | C-1 | C-2 | C-3 | C-4 | C-5 | C-6 |
| (a) | Anionic Surfactant | SODIUM COCOYL ISETHIONATE | 9.4 | 9.4 | 9.4 | 9.4 | 9.4 | 9.4 | | 9.4 |
| | | POTASSIUM COCOATE | 0.2 | 0.2 | 0.23 | 0.23 | 0.23 | 0.23 | 0.2 | |
| | | POTASSIUM COCOYL GLYCINATE | 0.5 | 0.5 | 0.5 | 0.5 | 0.5 | 0.5 | 0.5 | |
| | Total Anionic Surfactants | | 10 | 10 | 10 | 10 | 10 | | 10 | 10 |
| (b) | Amphoteric Surfactants | COCAMIDOPROPYL BETAINE COCO-BETAINE | 2.6 | 2.6 | 2.6 | 2.6 | 2.6 | 2.6 | 2.6 | 2.6 |
| (c) | Nonionic Surfactant | DECYL GLUCOSIDE | 8.5 | 8.5 | 8.5 | 8.5 | 8.5 | 8.5 | 8.5 | 8.5 |
| | | PEG-55 PROPYLENE GLYCOL OLEATE, PEG-150 DISTEARATE, AND PPG-5-CETETH-20 | 1.3 | 1.3 | 1.2 | 1.2 | 1.2 | 1.2 | 1.3 | 1.3 |
| | Total Surfactants | | 22.3 | 22.3 | 22.3 | 22.3 | 22.3 | 22.3 | 22.3 | 22.3 |
| (d) | HYDROXYPROPYL GUAR HYDROXYPROPYLTRIMONIUM CHLORIDE | | 0.5 | 0.5 | | | 0.5 | | 0.5 | 0.5 |
| | GUAR HYDROXYPROPYLTRIMONIUM CHLORIDE | | | | 0.5 | 0.5 | | | | |
| (e) | Cationic Polymer | POLYQUATERNIUM-10 | 0.3 | 0.3 | 0.3 | | | 0.3 | 0.3 | 0.3 |
| | | POLYQUATERNIUM-7 | | | | 0.3 | | | | |
| (g) | Fatty Compounds | COCO-CAPRYLATE/CAPRATE | 0.2 | 0.2 | 0.2 | 0.2 | 0.2 | 0.2 | 0.2 | 0.2 |
| | | SHEA BUTTER | 0.1 | 0.1 | 0.1 | 0.1 | 0.1 | 0.1 | 0.1 | 0.1 |
| | | SUNFLOWER SEED OIL | | | | | | | | |
| | | AVOCADO OIL | 0.1 | 0.1 | 0.1 | 0.1 | 0.1 | 0.1 | 0.1 | 0.1 |
| | | GLYCOL DISTEARATE | 0.1 | 0.1 | 0.1 | 0.1 | 0.1 | 0.1 | 0.1 | 0.1 |
| (h) | Water-Soluble Solvent | PROPYLENE GLYCOL, AND/OR CAPRYLYL GLYCOL[1] | 0.8 | 0.8 | 0.8 | 0.8 | 0.8 | 0.8 | 0.8 | 0.8 |
| (i) | Non-Cationic Thickening Polymer | ACRYLATES/C10-30 ALKYL ACRYLATE CROSSPOLYMER | 0.1 | 0.3 | 0.1 | 0.1 | 0.3 | 0.3 | 0.3 | 0.3 |
| (j) | Misc.[2] | SORBITOL | 2 | 2 | 2 | 2 | 2 | 2 | 2 | 2 |
| | | HYDROXYETHYL UREA | 1.2 | 1.2 | 1.2 | 1.2 | 1.2 | 1.2 | 1.2 | 1.2 |
| | | Preservatives, fragrances, pH adjusters, salts, chelating agents, buffers, amino acids, composition colorants, fillers (such as talc, calcium carbonate, silica, including hydrated silica), vitamins, botanical extracts, etc. | ≤5 | ≤5 | ≤5 | ≤5 | ≤5 | ≤5 | ≤5 | ≤5 |
| (f) | | WATER | 70.4 | 69.9 | 70.6 | 70.6 | 70.1 | 70.4 | 79.3 | 70.6 |

[1]Capryl glycol is shown in the table as a water soluble solvent. It also provides preservative attributes to the compositions. Therefore, it may also be characterized as a preservative.

[2]For example, fragrance, potassium hydroxide, tocopherol, sodium benzoate, sodium chloride, rosemary leaf extract, citric acid, salicylic acid, fumaric acid, glycine, etc.

Example 2

Combing Force Study

The compositions of Example 1 were compared to determine how combinations of different cationic polymers influence hair cleansed with the compositions. Highly bleached Caucasian hair swatches (SA40, 2.7 g, 27 cm) were obtained from a commercial supplier. All hair swatches were initially cleansed with the same standard shampoo. After rinsing the standard shampoo from the hair swatches, the hair swatches were cleansed with one of the compositions set forth in Example 1. The same amount of each composition (A, B, and C) was applied to hair swatches, lathered into the hair swatches, and rinsed from the hair swatches. After rinsing, excess water was removed from the hair swatches with a dry towel. The cleansed hair swatches were evaluated with a Dia-Stron Fibre One instrument, commonly used in industry to evaluate wet combing force. A comb having a 5 mm gap was run through the hair swatches beginning at the root end of the hair swatches (70 mm from the root end of the hair swatches) along a length of 200 mm, at a speed of 20 mm/sec. The measurement was repeated 5 times per swatch, the average calculated, and reported as total wet combining force (gf*mm) as shown below in Table II.

TABLE II

| | A | C-1 | C-2 |
|---|---|---|---|
| Total Wet Combing Force (gf*mm) | 1745333 | 2975597 | 2260385 |

Hair swatches cleansed with Inventive Composition A required significantly less combining force than hair cleansed with Comparative Compositions C-1 and C-2. These cleansing compositions differ with respect to the combination of cationic polymers but are otherwise identical. Therefore, the data show that hydroxypropyl guar hydroxypropyltrimonium chloride is unique when combined with a cationic cellulose. Polyquaternium-10 is a cationic cellulose (quaternized hydroxyethyl cellulose). Combing force was not reduced for hair treated with Comparative Composition C-1, containing a combination of polyquaternium-10 and guar hydroxypropyltrimonium chloride. Similarly, combing force was not reduced for hair treated with Comparative Composition C-2, containing a combination of hydroxypropyl guar hydroxypropyltrimonium chloride and polyquaternium-7. Polyquaternium-7 is a copolymer of acrylamide and diallyldimethylammonium chloride, not a cationic cellulose. It was surprising to find that a combination of hydroxypropyl guar hydroxypropyltrimonium chloride and a cationic cellulose provide such significant improvements to hair with respect to ease of combing (reduced combing force).

Example 3

Cosmetic Properties

Inventive Composition B and Comparative Compositions C-3, C-4, C-5, and C-6 were tested and compared to determine the cosmetic benefits provided by the compositions. Specifically, the following characteristics were assessed: Maximum Foam Height (mm), Foam Height at 180 seconds (3 minutes) (mm), Percent Foam Endurance (%), Maximum Wet Combing Force (gram force (gf)), Curl Definition, and Frizz Control.

Maximum Foam Height was obtained by measuring the highest point of the foam height with a foam analyzer (KRUSS Dynamic Foam Analyzer DFA100) immediately after mixing an aqueous solution of the composition at about 25° C. for 20 seconds at 4000 rpm. 2.5 grams of the compositions were combined with 47.5 grams of water (total of 50 grams of solution). After mixing the solutions at about 25° C. for 20 seconds at 4000 rpm, the foam analyzer measured the maximum foam height and lastingness of the foam.

Foam Height at 180 seconds (3 minutes) immediately after the mixing described above ceased was measured. The solutions were not agitated during the 180 seconds. The highest point of the foam height was again measured.

Percent Foam Endurance (PFE) was calculated with the following equation:

$$PFE\ (\%) = (\text{Foam Height at 180 seconds/Maximum Foam Height}) \times 100$$

Maximum Wet Combing Force was determined as follows. Highly bleached Caucasian hair swatches (SA40, 2.7 g, 27 cm) were obtained from a commercial supplier. All hair swatches were initially cleansed with the same standard shampoo. After rinsing the standard shampoo from the hair swatches, the hair swatches were cleansed with Inventive Composition B, Comparative Compositions C-3, C-4, C-5, or C-6. The same amount of each composition was applied to the hair swatches, lathered into the hair swatches, and rinsed from the hair swatches. After rinsing, excess water was removed from the hair swatches with a dry towel. The cleansed hair swatches were evaluated with a Dia-Stron Fibre One instrument, commonly used in industry to evaluate wet combing force. A comb having a 5 mm gap was run through the hair swatches beginning at the root end of the hair swatches (70 mm from the root end of the hair swatches) along a length of 200 mm, at a speed of 20 mm/see and the Maximum Wet Combing Force ascertained. The Maximum Wet Combing Force is the highest combing force reached as the comb was run through the hair swatches.

Curl Definition and Degree of Frizz were visually evaluated by a panel of 3 experts on a scale of 1 to 5 (described below) and the scored averaged.

1 Better than Inventive Composition B
2 Slightly better than Inventive Composition B
3 Same as Inventive Composition B
4 Slightly inferior to Inventive Composition B
5 Inferior to Inventive Composition B The results are reported in the Table III, below, and pictures of the tested swatches presented in The FIGURE.

TABLE III

| | B | C-3 | C-4 | C-5 | C-6 |
|---|---|---|---|---|---|
| Maximum Foam Height (mm) | 91 | 102 | 88 | 100 | 83 |
| Foam Height at 180 s after mixing (mm) | 61 | 82 | 48 | 66 | 43 |
| Percent Foam Endurance (%) | 67 | 80 | 55 | 66 | 52 |
| Maximum Wet Combing Force (gf*mm) | 34.4 | 35.5 | 62.1 | 52.4 | 36.6 |
| Curl Definition | NA | 4 | 5 | 4 | 5 |
| Frizz Control | NA | 5 | 5 | 4 | 3 |

The data show that Inventive Composition B provided a surprising drop in Maximum Wet Combing Force, due at least in part to inclusion of the hydroxypropyl guar hydroxypropyltrimonium chloride. This means that hair cleansed with Inventive Composition B is much easier to comb through, especially when wet. Comparison with Comparative Composition C-4 is particularly useful for showing the criticality of the hydroxypropyl guar hydroxypropyltrimonium chloride, as Comparative Composition C-4 exhibited the highest Maximum Wet Combing Force (and lacked hydroxypropyl guar hydroxypropyltrimonium chloride). Comparative Composition C-4 was the most difficult to comb through.

It was also surprising to discover that the acyl isethionate surfactants contribute to the improvement for Maximum Wet Combing Force, as evidenced by the results for Comparative Composition C-5. It was assumed that anionic surfactants would have the opposite effect, due to their cleansing properties. The data show that the acyl isethionate surfactant, in the compositions of the instant case, improved the conditioning properties. This is contrary to the understanding (and expectation) that the cleansing effects of the anionic surfactant would reduce the conditioning effects provided by cationic conditioning polymers in the compositions.

The data show that Inventive Composition B had excellent foaming properties despite containing both anionic surfactants (e.g., sodium cocoyl isethionoate) and cationic polymers (hydroxypropyl guar hydroxypropyltrimonium chloride and polyquaternium-10).

Without wishing to be bound by a particular theory, the inventor believes the foaming properties of C-3 are better than Inventive Composition B because Comparative Composition C-3 lacks polyquaternium-10 (a cationic cellulose), which interacts with the anionic surfactants. Absent the cationic polymer, fewer "neutralizing" interaction occur and therefore more foam is generated. However, curl definition and frizz control properties suffer, as shown by Comparative Composition C-3. Thus, results for Comparative Composition C-3 show the criticality of a cationic cellulose.

Similarly, the inventor believes the foaming properties of C-5 are better than Inventive Composition B because Comparative Composition C-5 lacks sodium cocoyl isethionate (an anionic surfactant), which interacts with the cationic polymers. Absent the "neutralizing" interaction, between the anionic surfactant and cationic polymers, more foam is generated. However, curl definition and frizz control properties suffer, as shown by the results for Comparative Composition C-5. This is surprising because it was expected that removal of the anionic surfactant would provide better conditioning properties given that anionic surfactants are known to reduce the conditioning effects provided by cationic conditioning polymers. Anionic surfactants serve to cleanse the hair and remove residue, including oils, which naturally condition the hair. Thus, it is common to use a separate conditioning product after cleansing the hair with a cleansing composition. Surprisingly, the compositions of the instant case not only cleanse but also simultaneously impart conditioning benefits to the hair.

In sum, Inventive Composition B provided exceptional foaming properties despite the inclusion of two cationic polymers. In addition, Inventive Composition B provided surprisingly superior conditioning qualities to the hair. Omission of the hydroxypropyl guar hydroxypropyltrimonium chloride (Comparative Composition C-4) or omission of the acyl isethionate surfactant (Comparative Composition C-5), resulted in a loss of the superior conditioning properties provided by Inventive Composition B.

The foregoing disclosure illustrates and describes embodiments of the invention. The disclosure shows and describes only the preferred embodiments, but it is understood that the invention is useable in various other combinations, modifications, and environments and is capable of changes or modifications within the scope of the inventive concepts as expressed herein, commensurate with the above teachings and/or the skill or knowledge of the relevant art. The embodiments described herein above are further intended to explain best modes known by applicant and to enable others skilled in the art to utilize the disclosure. Accordingly, the description is not intended to limit the invention.

As used herein, the terms "comprising," "having," and "including" (or "comprise," "have," and "include") are used in their open, non-limiting sense. The phrase "consisting essentially of" limits the scope of a claim to the specified materials or steps and those that do not materially affect the basic and novel characteristics of the claimed invention.

The terms "a," "an," and "the" are understood to encompass the plural as well as the singular.

Thus, the term "a mixture thereof" or "a combination thereof" also relates to "mixtures thereof" or "combinations thereof." Throughout the disclosure, the term "a combination thereof" may be used following a list of elements as shown in the following example where letters A-F represent the elements: "one or more elements selected from the group consisting of A, B, C, D, E, F, and a combination thereof." The term, "a combination thereof" does not require that the combination include all of A, B, C, D, E, and F (although all of A, B, C, D, E, and F may be included). Rather, it indicates that a combination of any two or more of A, B, C, D, E, and F can be included. In other words, it is equivalent to the phrase "one or more elements selected from the group consisting of A, B, C, D, E, F, and a combination of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a combination thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The salts referred to throughout the disclosure may include salts having a counter-ion such as an alkali metal, alkaline earth metal, or ammonium counterion. This list of counterions, however, is non-limiting.

The expression "one or more" means "at least one" and thus includes individual components as well as mixtures/combinations.

The term "plurality" means "more than one" or "two or more."

The term "cationic cellulose" is interchangeable with the term "cationic cellulose-derived polymer," "cationic cellulose-based polymer," or "cationic derivative of cellulose." Cellulose itself is the main constituent of plant cell walls and of vegetable fibers such as cotton. It is a polysaccharide consisting of chains of glucose monomers and is not cationic. Therefore, cellulose itself is not a cationic cellulose, but can be useful as a non-cationic thickening polymer.

The term "cationic guar" is interchangeable with the "cationic guar-derived polymer," "cationic guar-based polymer," or "cationic derivative of guar." Guar itself is typically referred to a "guar gum" and is called "guaran." It is a galactomannan polysaccharide extracted from guar beans that has thickening and stabilizing properties. Therefore, guar (guar gum or guaran) itself is not a cationic guar, but can be useful as a non-cationic thickening polymer.

Other than in the operating examples, or where otherwise indicated, all numbers expressing quantities of ingredients and/or reaction conditions can be modified in all instances by the term "about," meaning within +/−5% of the indicated number.

Some of the various categories of ingredients identified for the cleansing compositions may overlap. In such cases where overlap may exist and the composition/product includes two overlapping ingredients (or more than two overlapping ingredients), an overlapping ingredient does not represent more than one component. For example, a fatty ester may be defined as both a "fatty compound" and separately as a "surfactant." If a particular claimed composition/product includes both a fatty compound and a surfactant, a single fatty ester in the composition can serve as only the fatty compound or as only the surfactant (it cannot singularly qualify as both the fatty compounds and the surfactant).

All percentages, parts, and ratios herein are based upon the total weight of the compositions of the present invention, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically 1, 2, 3, 4 and 5, as well as sub ranges such as 2-5, 3-5, 2-3, 2-4, 1-4, etc.

The term "surfactant" includes salts of the surfactant, to the extent they exist, even if not explicitly stated. In other words, whenever the disclosure refers to a surfactant (or surfactants), it is intended that salts of the surfactants are also encompassed to the extent such salts exist, even though the specification may not specifically refer to a salt (or may not refer to a salt in every instance throughout the disclosure), for example, by using language such as "a salt thereof" or "salts thereof." Sodium and potassium are common cations that form salts with surfactants. However, additional cations such as ammonium ions, or alkanolammonium ions such as monoethanolammonium or triethanolammonium ions, may also form salts of surfactants.

All components positively set forth in the instant disclosure can be negatively excluded. In other words, the cleansing compositions of the instant disclosure may be free or essentially free of any one or more of the components positively set forth in the instant disclosure.

The term "substantially free" or "essentially free" as used herein means the specific material may be present in small amounts that do not materially affect the basic and novel characteristics of the claimed invention. For example, there may be less than 1% by weight of a specific material added to a composition, based on the total weight of the compositions (provided that an amount of less than 1% by weight does not materially affect the basic and novel characteristics of the claimed invention). Similarly, when a composition is essentially free from a particular element, the composition may include less than 1 wt. %, less than 0.5 wt. %, less than 0.1 wt. %, less than 0.05 wt. %, or less than 0.01 wt. %, or none of the specified material. Furthermore, all components that are positively set forth in the instant disclosure may be essentially excluded from the claims, e.g., a claimed composition may be "free," "essentially free" (or "substantially free") of one or more components that are positively set forth in the instant disclosure.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A cleansing composition comprising:

(a) about 5 to about 20 wt. % of a plurality of anionic surfactants comprising:

(a)(i) one or more acyl isethionates, salts thereof, or combination thereof; and (a)(ii) one or more acyl amino acids, salts thereof, or combination thereof;

(b) about 1 to about 10 wt. % of one or more amphoteric surfactants;

(c) about 1 to about 15 wt. % of one or more nonionic surfactants;

wherein (a), (b), and (c) are in an amount totaling about 15 to about 40 wt. % of the composition, (d) about 0.1 to about 5 wt. % of hydroxypropyl guar hydroxypropyltrimonium chloride;

(e) one or more cationic polymers other than a cationic guar, wherein at least one of the one or more cationic polymer is a cationic cellulose; and (f) water;

wherein all percentages by weight are based on a total weight of the cleansing composition.

2. The cleansing composition of claim 1, wherein the one or more acyl isethionates, salts thereof, or combination thereof are selected from sodium isethionate, sodium cocoyl isethionate, sodium lauroyl methyl isethionate, sodium cocoyl methyl isethionate, salts thereof, or a combination thereof.

3. The cleansing composition of claim 1, wherein the one or more acyl amino acids, salts thereof, or combination thereof are selected from acyl taurates, acyl glycinates, acyl glutamates, and acyl sarcosinates, salts thereof, or a combination thereof.

4. The cleansing composition of claim 3, wherein at least one of the one or more acyl amino acids, salts thereof, or combination thereof is an acyl glycinate, salt thereof, or combination thereof.

5. The cleansing composition of claim 4, wherein the acyl glycinate, salt thereof, or combination thereof, is selected from sodium cocoyl glycinate, sodium lauroyl glycinate, sodium myristoyl glycinate, potassium lauroyl glycinate, potassium cocoyl glycinate, salts thereof, or a combination thereof.

6. The cleansing composition of claim 1, wherein the cleansing composition is essentially free from anionic sulfate-based surfactants.

7. The cleansing composition of claim 1, wherein the one or more amphoteric surfactants are selected from alkyl amphoproprionates, betaines, alkyl sultaines, alkyl amphoacetates, or a combination thereof.

8. The cleansing composition of claim 7, wherein at least one of the one or more amphoteric surfactants is a betaine.

9. The cleansing composition of claim 8, wherein the betaine is selected from coco betaine, cocamidopropyl betaine, lauryl betaine, laurylhydroxy sulfobetaine, lauryldimethyl betaine, cocamidopropyl hydroxysultaine, behenyl betaine, capryl/capramidopropyl betaine, lauryl hydroxysultaine, stearyl betaine, or a combination thereof.

10. The cleansing composition of claim 1, wherein at least one of the one or more nonionic surfactants is an alkyl polyglucoside.

11. The cleansing composition of claim 10, wherein the alkyl polyglucoside is selected from lauryl glucoside, octyl glucoside, decyl glucoside, coco glucoside, caprylyl/capryl glucoside, or a combination thereof.

12. The cleansing composition of claim 1, wherein the cationic cellulose is selected from polyquaternium-4, polyquaternium-10, polyquaternium-24, polyquaternium-67, or a combination thereof.

13. The cleansing composition of claim 1, further comprising about 0.1 to about 5 wt. % of one or fatty compounds.

14. The cleansing composition of claim 1, further comprising about 0.1 to about 15 wt. % of one or more water-soluble solvents.

15. The cleansing composition of claim 1, further comprising about 0.1 to about 5 wt. % of one or more non-cationic thickening polymers.

16. The cleansing composition of claim 15, wherein the one or more non-cationic thickening polymers are selected from polyacrylate, polymethacrylate, polyethylacrylate, polyacrylamide, acrylic acid/acrylonitrogen copolymer, acrylates/steareth-20 itaconate copolymer, acrylates/ceteth-20 itaconate copolymer, acrylates/aminoacrylates/C10-30 Alkyl PEG-20 Itaconate copolymer, acrylates/aminoacrylates copolymer, acrylates/steareth-20 methacrylate copolymer, acrylates/beheneth-25 methacrylate copolymer, acrylates/steareth-20 methacrylate crosspolymer, acrylates/beheneth-25 methacrylate/HEMA crosspolymer, acrylates/vinyl neodecanoate crosspolymer, acrylates/vinyl isodecanoate crosspolymer, acrylates/palmeth-25 acrylate copolymer, acrylic acid/acrylamidomethyl propane sulfonic acid copolymer, acrylates/C10-C30 alkyl acrylate crosspolymer, carbomers, hydrophobically modified polypolyacrylates, hydrophobically modified polyacrylic acids, hydrophobically modified polyacrylamides, acrylamide/ammonium acrylate copolymer, acrylamide/sodium acryloyldimethyl taurate copolymer/isohexadecane/polysorbate 80, ammonium acryloyldimethyltaurate/VP copolymer, sodium acrylate/sodium acryloyldimethyl taurate copolymer, acrylates copolymer, acrylates crosspolymer-4, acrylates crosspolymer-3, acrylates/beheneth-25 methacrylate copolymer, acrylates/steareth-20 itaconate copolymer, ammonium polyacrylate/Isohexadecane/PEG-40 castor oil, sodium carbomer, crosslinked polyvinylpyrrolidone (PVP), polyacrylamide/C13-14 isoparaffin/laureth-7, polyacrylate-13/polyisobutene/polysorbate 20, polyacrylate crosspolymer-6, polyamide-3, acrylamide/sodium acryloyldimethyltaurate/acrylic acid copolymer, sodium acrylate/acryloyldimethyltaurate, sodium polyacrylate, or a combination thereof.

17. A cleansing composition comprising:

(a) about 5 to about 15 wt. % of a plurality of anionic surfactants comprising:

(a)(i) about 5 to about 15 wt. % of one or more acyl isethionates, salts thereof, or combination thereof; and (a)(ii) about 0.1 to about 5 wt. % of one or more acyl amino acids, salts thereof, or combination thereof;

(a)(iii) optionally, one or more additional anionic surfactants;

(b) about 1 to about 10 wt. % of one or more betaines;

(c) about 5 to about 15 wt. % of one or more nonionic surfactants, wherein at least one of the one or more nonionic surfactants is a polyglucoside in an amount of at least 5 wt. %;

wherein a total amount of (a), (b), and (c) is about 15 to about 30 wt. %, (d) about 0.1 to about 5 wt. % of hydroxypropyl guar hydroxypropyltrimonium chloride;

(e) about 0.1 to about 5 wt. % of one or more cationic celluloses selected from polyquaternium-4, polyquaternium-10, polyquaternium-24, polyquaternium-67, or a combination thereof;

(f) about 60 to about 85 wt. % of water;

(g) about 0.1 to about 5 wt. % of one or fatty compounds;

(h) about 0.1 to about 15 wt. % of one or more water-soluble solvents;

(i) about 0.1 to about 5 wt. % of one or more non-cationic thickening polymers; and (j) optionally, about 0.1 to about 10 wt. % of one or more miscellaneous ingredients;

wherein all percentages by weight are based on a total weight of the cleansing composition.

18. A method for cleansing hair comprising applying the cleansing composition of claim 1 to the hair and rinsing the cleansing composition from the hair.

19. The method of claim 18, wherein wet or damp hair cleansed with the cleansing composition requires less combing force to detangle than hair cleansed with a comparative cleansing composition without the hydroxypropyl guar hydroxypropyltrimonium chloride but otherwise identical to the cleansing composition.

20. The cleansing composition of claim 17, wherein the one or more non-cationic thickening polymers comprise acrylates/C10-C30 alkyl acrylate crosspolymer.

* * * * *